(12) United States Patent
Chen et al.

(10) Patent No.: US 6,923,800 B2
(45) Date of Patent: Aug. 2, 2005

(54) OSMOTIC DELIVERY SYSTEM, OSMOTIC DELIVERY SYSTEM SEMIPERMEABLE BODY ASSEMBLY, AND METHOD FOR CONTROLLING DELIVERY RATE OF BENEFICIAL AGENTS FROM OSMOTIC DELIVERY SYSTEMS

(75) Inventors: Guohua Chen, Sunnyvale, CA (US); Scott D. Lautenbach, San Mateo, CA (US); Keith E. Dionne, Cambridge, MA (US); Scott D. Jordan, Davis, CA (US); Steve A. Berry, Hollister, CA (US); Craig I. Rodenberger, San Jose, CA (US); Rupal Ayer, Santa Clara, CA (US)

(73) Assignee: ALZA Corporation, Mountain View, CA (US)

( * ) Notice: Subject to any disclaimer, the term of this patent is extended or adjusted under 35 U.S.C. 154(b) by 212 days.

(21) Appl. No.: 09/859,428

(22) Filed: May 18, 2001

(65) Prior Publication Data

US 2001/0027311 A1 Oct. 4, 2001

Related U.S. Application Data

(63) Continuation of application No. 09/121,878, filed on Jul. 24, 1998, now Pat. No. 6,287,295.
(60) Provisional application No. 60/053,689, filed on Jul. 25, 1997.

(51) Int. Cl.$^7$ ................................................ A61K 9/22
(52) U.S. Cl. .................................................. 604/892.1
(58) Field of Search .......................... 604/890.1, 891.1, 604/892.1; 424/422, 423, 424, 425

(56) References Cited

U.S. PATENT DOCUMENTS 3,732,865 A    5/1973    Higuchi et al.
3,987,790 A    10/1976   Eckenhoff et al.
3,995,631 A    12/1976   Higuchi et al.
3,995,632 A    12/1976   Nakano et al.

(Continued)

FOREIGN PATENT DOCUMENTS

| EP | 0 373 867 A | 6/1990 |
|---|---|---|
| WO | WO 92 00728 A | 1/1992 |
| WO | WO 97 27840 A | 8/1997 |

OTHER PUBLICATIONS

International Search Report, dated Feb. 3, 1999.

*Primary Examiner*—Manuel Mendez
(74) *Attorney, Agent, or Firm*—TraskBritt, PC

(57) ABSTRACT

Osmotic delivery system semipermeable body assemblies that control the delivery rate of a beneficial agent from an osmotic delivery system incorporating one of the semipermeable body assemblies are provided. A semipermeable body assembly or plug includes a semipermeable body which is positionable in an opening of an osmotic delivery system. The semipermeable body has a hollow interior portion having a size selected to obtain a predetermined liquid permeation rate through the semipermeable body. Because the beneficial agent in the osmotic delivery system is delivered at substantially the same rate, the osmotic agent imbibes liquid which has permeated through the plug from a surrounding environment, and the liquid permeation rate through the plug controls the delivery rate of the beneficial agent from the osmotic delivery system. The liquid permeation rate through a semipermeable body may be varied to control the delivery rate of beneficial agent from an osmotic delivery system by changing the thickness of the semipermeable body or by changing an amount of surface area of the semipermeable body that is exposed to liquid when the osmotic delivery system is located in a liquid environment of use.

32 Claims, 16 Drawing Sheets

U.S. PATENT DOCUMENTS

| | | |
|---|---|---|
| 4,111,202 A | 9/1978 | Theeuwes |
| 4,243,030 A | 1/1981 | Lynch et al. |
| 4,340,054 A | 7/1982 | Michaels |
| 4,373,527 A | 2/1983 | Fischell |
| 4,439,196 A | 3/1984 | Higuchi |
| 4,490,256 A * | 12/1984 | Nussbaumer et al. ....... 210/359 |
| 4,552,561 A | 11/1985 | Eckenhoff et al. |
| 4,639,244 A | 1/1987 | Rizk et al. |
| 4,865,845 A | 9/1989 | Eckenhoff et al. |
| 4,874,388 A | 10/1989 | Wong et al. |
| 5,209,746 A | 5/1993 | Balaban et al. |
| 5,223,265 A | 6/1993 | Wong |
| 5,279,608 A | 1/1994 | Cherif Cheikh |
| 5,308,348 A | 5/1994 | Balaban et al. |
| 5,312,389 A | 5/1994 | Theeuwes et al. |
| 5,312,390 A | 5/1994 | Wong |
| 5,456,679 A * | 10/1995 | Balaban et al. .......... 604/892.1 |
| 5,653,688 A | 8/1997 | Mills et al. |
| 5,690,952 A * | 11/1997 | Magruder et al. .......... 424/423 |
| 5,728,396 A * | 3/1998 | Peery et al. ................. 424/422 |

\* cited by examiner

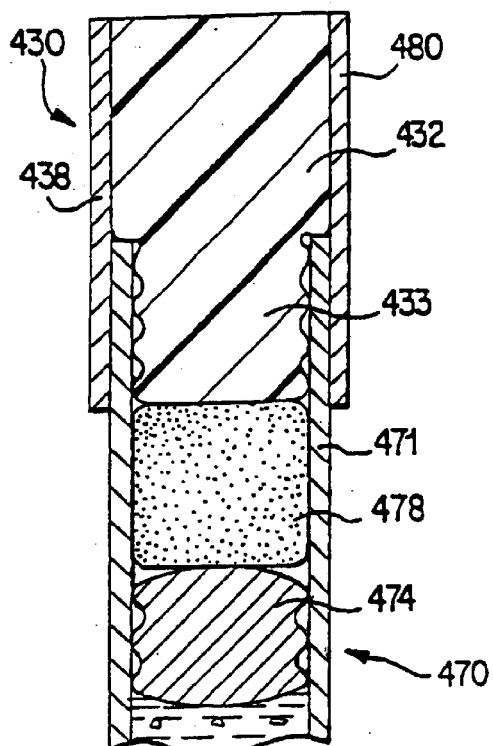
FIG. 15
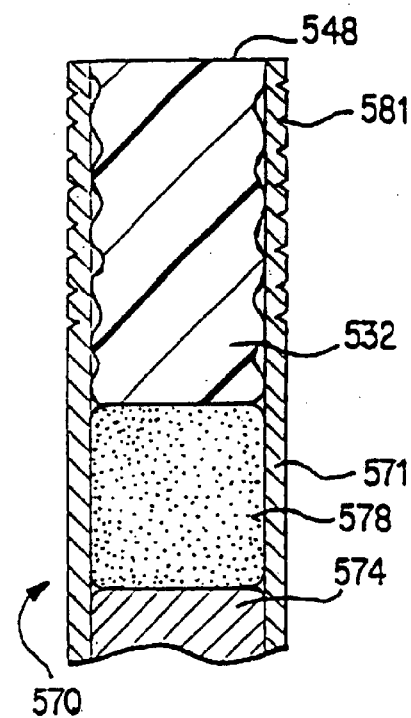
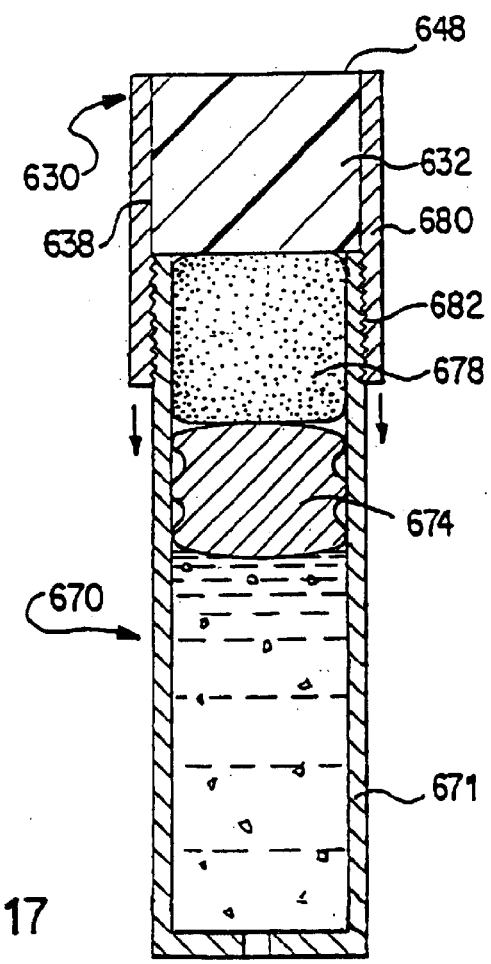
FIG. 17

OSMOTIC DELIVERY SYSTEM, OSMOTIC DELIVERY SYSTEM SEMIPERMEABLE BODY ASSEMBLY, AND METHOD FOR CONTROLLING DELIVERY RATE OF BENEFICIAL AGENTS FROM OSMOTIC DELIVERY SYSTEMS

CROSS-REFERENCE TO RELATED APPLICATIONS

This application is a continuation of U.S. patent application Ser. No. 09/121,878, filed Jul. 24, 1998, now U.S. Pat. 6,287,295, issued Sep. 11, 2001, which claims the benefit of U.S. Provisional Application No. 60/053,689 filed Jul. 25, 1997, pursuant to 35 U.S.C. § 119(e).

BACKGROUND OF THE INVENTION

1. Field of the Invention

The present invention relates generally to osmotic delivery systems for delivering beneficial agents, and more particularly, to osmotic delivery system semipermeable body assemblies which control the delivery rate of a beneficial agent from an osmotic delivery system incorporating one of the semipermeable body assemblies.

2. Description of the Related Art

Controlled delivery of beneficial agents, such as drugs, in the medical and veterinary fields has been accomplished by a variety of methods. One method for controlled prolonged delivery of beneficial agents involves the use of osmotic delivery systems. These devices can be implanted to release beneficial agents in a controlled manner over a preselected time or administration period. In general, osmotic delivery systems operate by imbibing liquid from the outside environment and releasing corresponding amounts of the beneficial agent.

FIG. 1 illustrates a cross-sectional view of a known osmotic delivery system 20. The osmotic delivery system 20, commonly referred to as an "osmotic pump," generally includes some type of a capsule or enclosure 22 having a semipermeable portion which may selectively pass water into an interior of the capsule which contains a water-attracting osmotic agent 24. In the known osmotic delivery system illustrated in FIG. 1, the walls of the capsule 22 are substantially impermeable to items within and outside the capsule, and the plug 26 acts as the semipermeable portion. The difference in osmolarity between the water-attracting agent 24 and the exterior of the capsule causes water to pass through the semipermeable portion of the capsule which in turn causes the beneficial agent 23 to be delivered from the capsule 22 through the delivery port 29. The water-attracting agent 24 may be the beneficial agent delivered to the patient; however, in most cases such as that illustrated in FIG. 1, a separate osmotic agent is used specifically for its ability to draw water into the capsule 22.

When a separate osmotic agent 24 is used, the osmotic agent may be separated from the beneficial agent 23 within the capsule 22 by a movable dividing member or piston 28. The structure of the capsule 22 is such that the capsule does not expand when the osmotic agent 24 takes in water and expands. As the osmotic agent 24 expands, it causes the beneficial agent 23 to be discharged through the delivery port 29 at the same rate as the liquid, which is typically water, enters the osmotic agent 24 by osmosis. Osmotic delivery systems may be designed to deliver a beneficial agent at a controlled constant rate, a varying rate, or in a pulsatile manner.

In the known osmotic delivery system 20 illustrated in FIG. 1, an osmotic tablet is used as the osmotic agent 24 and is placed inside the capsule 22. The membrane plug 26 is placed in an opening in the capsule 22 through which the osmotic agent 24 and piston 28 were inserted. Known membrane plugs 26 are typically a cylindrical member with ribs, and operate in the same manner as a cork. These membrane plugs 26 seal the interior of the capsule from the exterior environment, essentially permitting only certain liquid molecules from the environment of use to permeate through the membrane plug into the interior of the capsule 22. The rate that the liquid permeates through the membrane plug 26 controls the rate at which the osmotic agent 24 expands and drives a desired concentration of beneficial agent 23 from the osmotic delivery system 20 through the delivery port 29. The rate of delivery of the beneficial agent from the osmotic delivery system 20 may be controlled by varying the permeability coefficient of the membrane plug 26.

By varying the permeability coefficient of the membrane plug 26, the liquid permeation rate through the membrane is controlled. Osmotic delivery systems requiring a high beneficial agent delivery rate typically use membrane plugs having high permeability coefficients. Osmotic delivery systems requiring a low beneficial agent delivery rate use membrane plugs having low permeability coefficients. The permeability coefficient is dependent on the particular material or combination of materials used in each membrane plug 26. Thus, the known osmotic delivery system 20 illustrated in FIG. 1, which includes a membrane plug 26, may control the delivery rate of the beneficial agent 23 by forming the same configuration plug 26 from different semipermeable materials having permeability coefficients corresponding to the desired beneficial agent delivery rate. One problem associated with obtaining different permeation rates in this manner is that a different membrane material must be used for every system which has a different desired beneficial agent delivery rate, requiring the purchase of many different membrane materials and manufacture of many different membrane plugs 26.

Although the osmotic delivery device illustrated in FIG. 1 delivers consistent and reproducible beneficial agent delivery rates, it is not possible to easily alter the beneficial agent release rate from the osmotic delivery device; a new membrane plug must be manufactured and incorporated into the device for each application. In many instances, it is desirable to easily increase or decrease the beneficial agent release rate from the osmotic delivery device. For example, the release rate for some drugs should be increased or decreased for osmotic delivery devices that are to be implanted if the patient is overweight or underweight. Additionally, many disease treatment regimens require dose titration to optimize therapeutic response to the beneficial agent, requiring that the beneficial agent release rate be adjusted in accordance with the patient's efficacious response. It is not possible to easily adjust the beneficial agent release rate from current osmotic delivery devices, such as that illustrated in FIG. 1.

Many osmotic delivery systems which use membrane plugs, such as that illustrated in FIG. 1, must administer beneficial agents at rapid delivery rates over a short period of time. These known systems use membrane materials having high permeability coefficients, i.e., high liquid uptake semipermeable materials. In general, high liquid uptake semipermeable materials are those that have greater than 60% water uptake, where % water uptake=100×(wet weight−dry weight)/dry weight. Thus, low uptake semipermeable materials have equal or less than 60% water uptake.

A dramatic problem associated with membrane plugs made from high liquid uptake semipermeable materials is that the membrane plug material has a tendency to absorb liquid and swell as the liquid from the surrounding environment permeates through the membrane. This is problematic because when the membrane plug overly swells, it exerts forces on the walls of the enclosure. Such forces may rupture the enclosure and allow the beneficial agent, osmotic agent or other items within the interior of the enclosure to escape to the environment of use. Furthermore, the membrane plug may become dislodged from the system, which is especially hazardous with implantable delivery systems. Because of biocompatibility and delivery rate considerations, high liquid uptake membrane materials often must be used in osmotic delivery systems destined for human implantation; consequently, there is a need for osmotic delivery systems having membrane plugs which remain intact in the capsule during all phases of delivery.

Even if the membrane plug does not dislodge from the capsule, some high liquid uptake membrane plugs permit the osmotic agent to leak from the capsule because the membrane materials are biologically unstable. For instance, some semipermeable membranes having high permeability coefficients, such as organic polymer membranes, are unstable in biological environments and may degrade over time, permitting fluids, crystals, or powder within the interior of the capsule to leak to the environment of use. In some instances, the osmotic agent within the capsule may be harmful to the recipients of implantable delivery systems, especially if released as a bolus, i.e., all at once at a single location.

To ensure that the high liquid uptake membrane plug remains intact within the delivery system capsule and seals the interior of the capsule from the environment of use, some osmotic delivery systems use glues or adhesives with such high liquid uptake membrane plugs to prevent the capsule from leaking and to ensure that the membrane plug remains in place. Besides adding a manufacturing step and increasing costs, applying an adhesive to the membrane plugs may problematically affect the rate of permeation.

Still another problem associated with these high uptake membrane plugs is that the enclosure of the osmotic delivery system must be made sufficiently strong to withstand the greater forces exerted on the enclosure walls when the membrane plug expands radially.

Because of the above-identified problems associated with current osmotic delivery system membrane plugs, it is costly and particularly difficult to administer beneficial agents from osmotic delivery systems at different desired delivery rates. Known membrane plug designs control the permeation rate of the membrane and the beneficial agent delivery rate of the osmotic delivery system by selecting a different material membrane plug for each application requiring a particular beneficial agent administration rate. Additionally, current high liquid uptake membrane plugs may dislodge or leak, and may be unstable in biological environments, causing items in the interior of the delivery capsule to harmfully leak to the environment of use. These problems associated with current osmotic drug delivery systems having known membrane plugs have created a need for a solution.

SUMMARY OF THE INVENTION

One object of the present invention is to provide an osmotic delivery system semipermeable body assembly which controls the liquid permeation rate through the semipermeable body assembly by varying the size of a hollow interior portion or recess within the semipermeable body of the semipermeable body assembly.

Another object of the present invention is to provide an osmotic delivery system semipermeable body assembly which lessens the need to use high liquid uptake semipermeable materials for the membrane body of the semipermeable body assembly.

Another object of the present invention is to provide an osmotic delivery system semipermeable body assembly which permits relatively fast liquid permeation rates through semipermeable body materials made from relatively low permeability coefficient materials.

Still another object of the present invention is to provide osmotic delivery system semipermeable body assemblies having adjustable liquid permeation rates, even though the semipermeable bodies of the assemblies are made from one semipermeable material.

Yet another object of the present invention is to provide an osmotic delivery system semipermeable body assembly which helps prevent leakage from the interior of an osmotic delivery system.

Another object of the present invention is to provide an osmotic delivery system semipermeable body assembly which lessens the need to use glues or adhesives to keep the items within the osmotic delivery system from leaking to the environment of use.

Another object of the present invention is to provide an osmotic delivery system which incorporates an osmotic delivery system semipermeable body assembly according to the present invention.

Still another object of the present invention is to provide a method of controlling the delivery rate of a beneficial agent from an osmotic delivery system that incorporates an osmotic delivery system semipermeable body assembly according to the present invention.

Another object of the present invention is to provide a method of changing or altering a liquid permeation rate through a semipermeable body of an osmotic delivery system.

Still another object of the present invention is to provide a method of easily changing a liquid permeation rate through a semipermeable body of an osmotic delivery system.

Yet another object of the present invention is to provide an osmotic system having a semipermeable body having a liquid permeation rate that may be easily changed.

Still another object of the present invention is to increase the liquid permeation rate through semipermeable bodies of osmotic delivery system semipermeable body assemblies by increasing the surface area of the semipermeable body that is immediately exposed to liquid when the osmotic delivery system is located in a liquid environment of use.

The present invention strives to address the disadvantages of known osmotic delivery systems by providing: an osmotic delivery system semipermeable body assembly or plug for controlling a delivery rate of a beneficial agent from an osmotic delivery system; an osmotic delivery system incorporating the plug; a method of controlling the delivery rate of a beneficial agent from an osmotic delivery system with the plug; a method of changing a liquid permeation rate through a semipermeable body of an osmotic delivery system to increase a delivery rate of a beneficial agent from the osmotic delivery system; a method of varying a liquid permeation rate through a semipermeable body of an osmotic delivery system; an osmotic delivery system having a semipermeable body and a liquid impermeable sleeve; and an osmotic delivery system having two abutting semipermeable bodies. Different liquid permeation rates through semipermeable membranes of the osmotic delivery systems according to embodiments of the present invention are obtainable by varying the thickness and/or the surface area of the semipermeable membrane that is immediately exposed to liquid when the osmotic delivery system is located in a liquid environment of use. Additionally, different desired liquid permeation rates through osmotic delivery system plugs according to embodiments of the present invention are obtainable from plugs formed from the same material having the same permeability coefficient and uptake characteristics.

The foregoing and other objects may be obtained by an osmotic delivery system plug that includes a semipermeable body. The semipermeable body has a recess having an interior surface beginning at an opening in the body and ending at a depth surface within the semipermeable body, a liquid contact surface located opposite the depth surface, and an outer surface located opposite the interior surface. The outer surface includes means for sealing an environment of use from an inside of an enclosure of an osmotic delivery system in which the body is insertable. The body also has a predetermined plug thickness defined by the location of the depth surface relative to the fluid surface, and a predetermined wall width defined by the location of the outer surface relative to the interior surface. At least one of the predetermined plug thickness and predetermined wall width control a rate of liquid permeation through the semipermeable body. The osmotic delivery system plug also includes an insert located within the recess.

The foregoing and other objects may be obtained by an osmotic delivery system plug that includes a semipermeable body at least partially positionable in an opening in an enclosure of an osmotic delivery system. The semipermeable body includes a hollow interior portion having a size selected to obtain a predetermined liquid permeation rate through the semipermeable body. The liquid permeation rate controls a delivery rate of a beneficial agent from an osmotic delivery system according to the present invention. The osmotic delivery plug may also include an insert.

The foregoing and other objects and advantages may be obtained by an osmotic delivery system that includes an enclosure having an opening and a delivery port. The enclosure also has an interior holding a liquid swellable osmotic agent and a beneficial agent. The liquid swellable osmotic agent is for imbibing liquid from a surrounding environment and causing a delivery rate of the beneficial agent from the enclosure. The osmotic delivery system includes a plug having a semipermeable body at least partially positioned in the opening. The semipermeable body includes a hollow interior portion having a size selected to obtain a predetermined liquid permeation rate through the semipermeable body. The liquid permeation rate is for controlling the delivery rate of the beneficial agent from the osmotic delivery system.

The foregoing and other objects and advantages may be obtained by a method of controlling a delivery rate of a beneficial agent from the aforementioned osmotic drug delivery system using the aforementioned osmotic delivery system plug, the method including the steps of: determining a desired delivery rate of the beneficial agent; selecting a plug with a hollow interior portion sized to obtain a predetermined liquid permeation rate through the semipermeable body corresponding to the desired delivery rate of the beneficial agent; positioning the plug at least partially within the opening of the enclosure; and locating the osmotic drug delivery system in an environment of use.

The foregoing and other objects and advantages may be obtained by a method of changing a liquid permeation rate through a semipermeable body of an osmotic delivery system to increase a delivery rate of a beneficial agent from the osmotic delivery system. The method includes the steps of making a semipermeable body having a liquid permeability coefficient and a thickness, and changing the thickness of the semipermeable body to alter a liquid permeation rate through the semipermeable body.

The foregoing and other objects and advantages may be obtained by a method of varying a liquid permeation rate through a semipermeable body of an osmotic delivery system in which a liquid impermeable sleeve is mounted on the semipermeable body to vary a delivery rate of a beneficial agent from the osmotic delivery system. The method includes the step of moving the liquid impermeable sleeve along an exterior surface of the semipermeable body to vary an amount of surface area of the exterior surface that is immediately exposed to liquids when the osmotic delivery system is located in a liquid environment of use.

The foregoing and other objects and advantages may be obtained by a method of varying a liquid permeation rate through a semipermeable body of an osmotic delivery system to vary a delivery rate of a beneficial agent from the osmotic delivery system. The method includes the step of selecting a desired liquid permeation rate through the semipermeable body of the osmotic delivery system, and providing a plurality of semipermeable body elements in abutting relation to one another to define the semipermeable body and to achieve the selected liquid permeation rate.

The foregoing and other objects and advantages may be obtained by an osmotic delivery system having a liquid impermeable enclosure having an interior holding a beneficial agent and an osmotic agent for imbibing liquid from a surrounding environment and causing delivery of the beneficial agent from the liquid impermeable enclosure. A semipermeable body is in liquid communication with the liquid impermeable enclosure for permitting liquid to permeate through the semipermeable body to the osmotic agent. A liquid impermeable sleeve separate from the liquid impermeable enclosure and surrounding a portion of a surface of the semipermeable body such that the portion of the surface is not immediately exposed to liquid when the osmotic delivery system is located in a liquid environment of use and such that the semipermeable body includes an exposure surface defined by an area of the surface that is not surrounded by the liquid impermeable sleeve and is immediately exposed to liquids when the osmotic delivery system is located in the liquid environment of use.

The foregoing and other objects and advantages may be obtained by an osmotic delivery system including an enclosure having an interior holding a beneficial agent and an osmotic agent. The osmotic agent is for imbibing liquid from a surrounding environment and causing delivery of the beneficial agent from the enclosure. A first semipermeable body is in liquid communication with the enclosure for permitting liquid to permeate through the first semipermeable body to the osmotic agent. A second semipermeable body abuts the first semipermeable body and is in liquid communication with the first semipermeable body so as to permit liquid to permeate through the first semipermeable body and the second semipermeable body to the osmotic agent.

The foregoing and other objects and advantages may be obtained by an osmotic delivery system having an enclosure.

The enclosure includes an opening, a delivery port, and an interior holding a liquid swellable osmotic agent and a beneficial agent. The liquid swellable osmotic agent is for imbibing liquid from a surrounding environment and causing a delivery rate of the beneficial agent from the enclosure. The osmotic delivery system includes a plug having a semipermeable body. The plug is at least partially positioned in the opening. The semipermeable body has an exposure surface that is immediately exposed to liquids when the osmotic delivery system is located in a liquid environment of use. The exposure surface includes a conical surface.

BRIEF DESCRIPTION OF THE DRAWINGS

The invention will be described in greater detail with reference to the accompanying drawings in which like elements bear like reference numerals, and wherein:

FIG. 15 is a partial sectional view of another osmotic delivery system according to the present invention having a semipermeable body and liquid impermeable sleeve, where the semipermeable body has been inserted into the enclosure and the enclosure is received by the liquid impermeable sleeve.

FIG. 16 is a partial sectional view of another osmotic delivery system according to the present invention having an enclosure with a plurality of grooves along which the enclosure and a semipermeable body may be cut.

FIG. 17 is a partial sectional view of another osmotic delivery system according to the present invention having a semipermeable body and liquid impermeable sleeve, where the liquid impermeable sleeve is threaded on the enclosure of the osmotic delivery system and is movable with respect to the semipermeable body.

FIG. 30 also illustrates the actual increase in the beneficial agent release rate of an osmotic delivery system according to the present invention, where the osmotic delivery system includes an osmotic delivery system semipermeable plug having a semipermeable body with a circular surface according to the present invention.

DESCRIPTION OF THE PREFERRED EMBODIMENT

The present invention generally relates to osmotic delivery system semipermeable body assemblies for controlling a delivery rate of a beneficial agent from osmotic delivery systems. FIGS. 7, 13–20, 25, and 28 each illustrate semipermeable body assemblies in cooperation with osmotic delivery systems according to the present invention.

FIGS. 2–6 illustrate features of an osmotic delivery system plug or semipermeable body assembly 30 according to one embodiment of the present invention. The osmotic delivery system plug 30 will be described in reference to an exemplary osmotic delivery system 70 according to one embodiment of the present invention illustrated in FIG. 7. The configuration of the osmotic delivery system plug 30 dictates the liquid permeation rate through the plug, which generally controls the delivery rate of a beneficial agent 72 from the osmotic delivery system 70.

Figure 2:
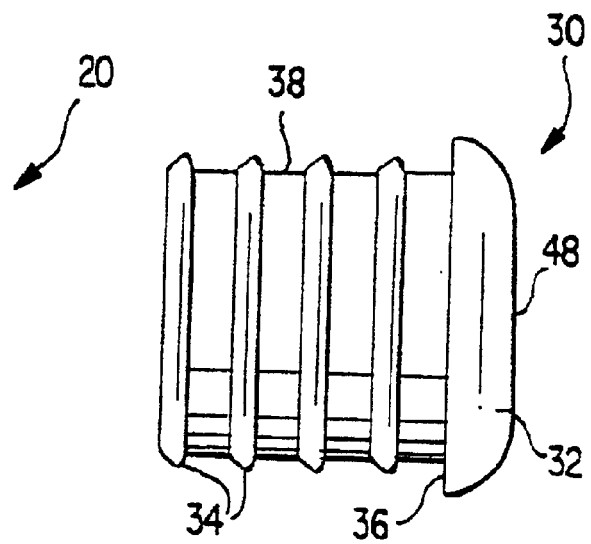
FIG. 2 is a side view of an osmotic delivery system plug or osmotic delivery system semipermeable body assembly according to the present invention.
Figure 3:
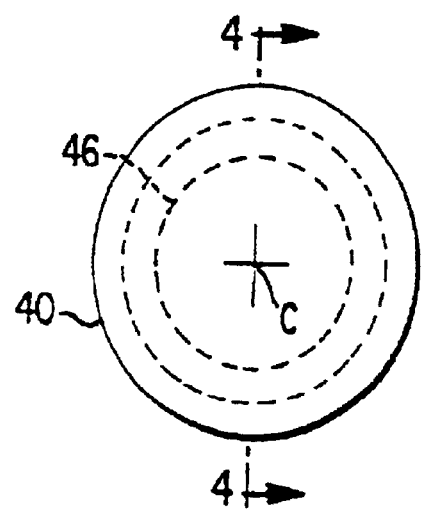
FIG. 3 is an end view of the osmotic delivery system plug of FIG. 2.

FIG. 2 illustrates a side view of the osmotic delivery system plug 30. The plug 30 is formed from a semipermeable body 32. The semipermeable body 32 is typically (but not necessarily) cylindrically shaped, and has means for sealing or ribs 34 extending out from the outer surface 38 of the plug. The ribs 34 are the means by which the plug operates like a cork or stopper, obstructing and plugging an opening 79 in a capsule or enclosure 71 of the osmotic delivery system 70 illustrated in FIG. 7. The means for sealing 34 may be the exemplary ribs, or may be other configurations such as threads, a tight interference fit between an outer sealing surface of the plug body 32 and the enclosure 71, glue, adhesives, ridges, lips, or other devices which join the body 32 with the enclosure 71 to prevent leakage. The plug body 32 is, therefore, intended for at least partial insertion into an opening 79 of an enclosure 71, and the means for sealing 34 the environment of use from an inside of the enclosure 71 prevents liquid and other substances in the environment of use, besides the permeation liquid, from entering the osmotic delivery system 70 while also preventing materials from the inside of the delivery system from leaking or escaping to the environment of use.

As mentioned above, the osmotic delivery system plug 30 is made from a semipermeable body 32, which is formed from a semipermeable material. The semipermeable material of the body 32 allows liquids, especially water, to pass from an exterior environment of use into the capsule or enclosure 71 to cause the osmotic agent 78 to swell. However, the semipermeable material forming the semipermeable body 32 is largely impermeable to the materials within the capsule and other ingredients within the fluid environment. Semipermeable compositions suitable for the semipermeable body 32 are well known in the art, examples of which are disclosed in U.S. Pat. No. 4,874,388, the entire disclosure of which is incorporated herein by reference.

Such possible semipermeable materials from which the body 32 can be made include, but are not limited to, for example, Hytrel polyester elastomers (DuPont), cellulose esters, cellulose ethers and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. By "degree of substitution," or "D.S.," is meant the average number of hydroxyl groups originally present on the anhydroglucose unit comprising the cellulose polymer that are replaced by a substituting group. Representative materials include, but are not limited to, one selected from the group consisting of cellulose acylate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and acetyl content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Other materials for the body 32 are polyurethane, polyetherblockamide (PEBAX, commercially available from ELF ATOCHEM, Inc.), injection-moldable thermoplastic polymers with some hydrophilicity such as ethylene vinyl alcohol (EVA). In general, the body 32 is made from semipermeable materials having a water uptake ranging from 1% to 80%, preferably less than 60%, but more preferably less than 50%. The composition of the semipermeable body 32 is permeable to the passage of external liquids such as water and biological liquids, and it is substantially impermeable to the passage of beneficial agents, osmopolymers, osmagents, and the like.

Figure 6:
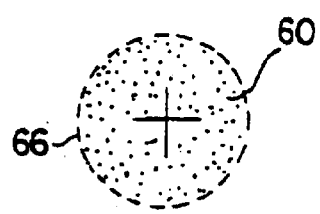
FIG. 6 is an end view of the insert of FIG. 5.
Figure 7:
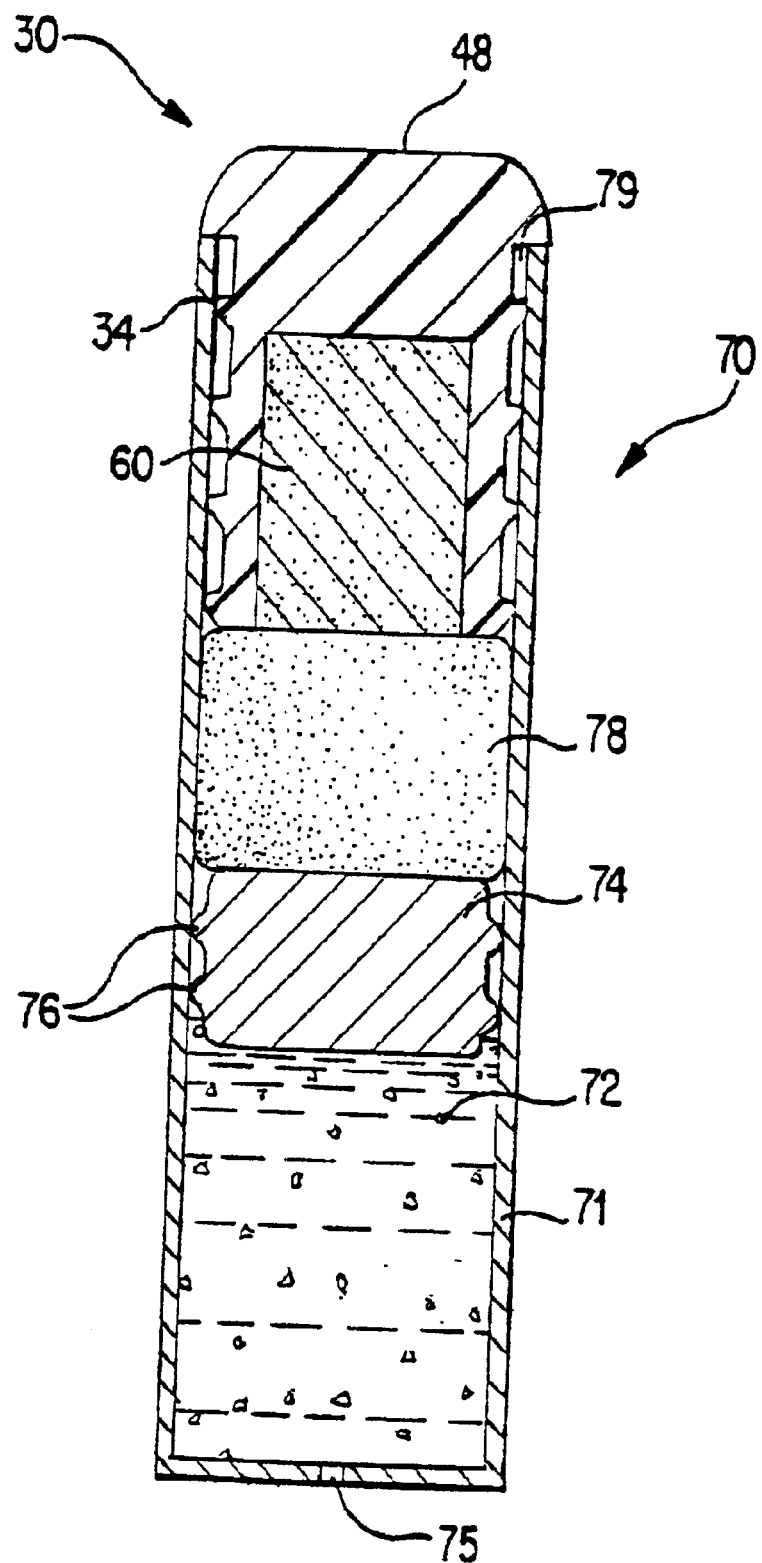
FIG. 7 is a sectional view of an osmotic delivery system according to the present invention.

As illustrated in FIGS. 2 and 7, the outer surface 38 of the semipermeable body 32 and the ribs 34 are meant for at least partial insertion in an osmotic delivery system opening 79. The plug 30 is insertable into the opening 79 until a stop surface 36 of the body 32 abuts the wall of the enclosure 71. Because at least a portion of the plug 30 is within the enclosure, and has means for sealing 34, only a portion of the plug and body 32 is exposed to liquids in the environment of use. In the embodiment of the present invention illustrated in FIGS. 2–7, the liquid contact surface 48 is the portion of the semipermeable body which is immediately exposed to liquids when the osmotic delivery system is placed in a liquid environment of use. Thus, as shown in FIG. 7, the liquid contact surface 48 is external of the enclosure 71, and the surface of the plug within the enclosure 71 is generally not immediately exposed to liquid when the osmotic delivery system is placed in a liquid environment of use. As shown in FIG. 2, the liquid contact surface 48 preferably has smoothed or curved corners which are more acceptable for implantation than sharp edges. Likewise, the outer diameter 40 of the liquid contact surface 48, measured about the longitudinal center axis C, is approximately equal to that of the enclosure 71 of the osmotic delivery system such that the interface between the enclosure and the liquid contact surface of the body 32 is void of abrupt edges, ridges, or sharp corners.

Figure 12:
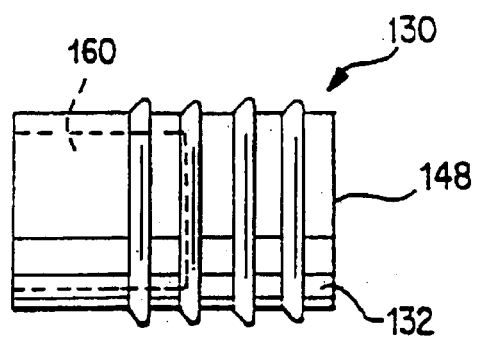
FIG. 12 is a side view of another osmotic delivery system plug according to the present invention.

Alternatively, the plug need not have a stop surface 36, as illustrated by the alternative embodiment of a plug or semipermeable body assembly 130 shown in FIG. 12. The foregoing and following discussion of the benefits and functions of the plug 30 also apply to the plug 130. Thus, the plug 130 is assigned corresponding reference numbers as the plug 30, increased by 100. The plug 130 also includes many additional features and inherent functions, as discussed below. The plug 130 may be inserted entirely within an opening of an enclosure of an osmotic delivery system because the plug 130 does not include a stop surface or head preventing complete insertion. When the plug 130 is completely inserted within the enclosure of an osmotic delivery system, the cylindrical flat surface or end surface 148 defines the liquid contact surface of the plug because it is immediately exposed to liquids when such an osmotic delivery system is placed in a liquid environment of use. The plug 130 may also be partially inserted into an opening of an osmotic delivery system enclosure such that the liquid contact surface includes more than just the end surface 148. The plug 130 includes a semipermeable body 132 that receives an insert 160, similar to the insert 60 described below.

Figure 4A:
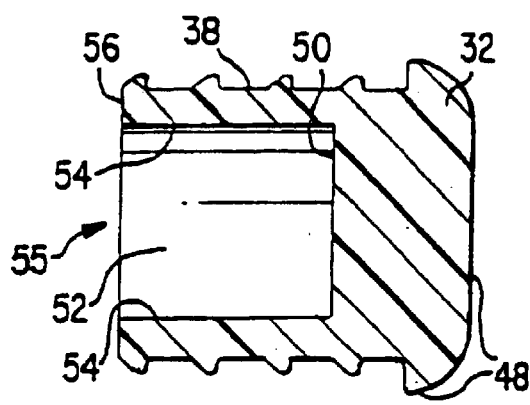
FIG. 4A is a sectional view of a semipermeable body of the osmotic delivery system plug according to the present invention taken along the line 4—4 of FIG. 3.

FIG. 4A depicts a cross-section of the semipermeable body 32. The semipermeable body 32 includes a hollow interior portion or recess 52. In the embodiment of the present invention depicted in FIG. 4A, the recess 52 is cylindrically shaped. The recess 52 has a cylindrical and longitudinal interior surface 54 which begins at an insert opening 55 formed by the recess in the insert end 56 of the semipermeable body 32, and ends at a depth surface 50 within the body 32. Because of the generally cylindrical shape of the outer surface 38 of the semipermeable body 32 and the cylindrical shape of the recess 52, the body is thimble or cup-shaped such that a "bottom of the cup" has a predetermined plug thickness t illustrated in FIG. 4B and the wall 57 has a predetermined wall width w, both further described below. In general, the semipermeable body 32 is cup-shaped because it is hollow, i.e., the semipermeable body 32 includes a cavity, gap, space, or concave indentation that defines a hollow area within the semipermeable body.

As shown in FIG. 4A, the predetermined wall width w is defined by the location of the outer surface 38 relative to the interior surface 54, and the predetermined plug thickness t is defined by the location of the depth surface 50 relative to the liquid contact surface 48. Thus, the depth of the depth surface 50 within the semipermeable body 32, and the distance the interior surface 54 is from the longitudinal center axis C (or diameter 46 of the recess 52), determine the size of the hollow interior portion or recess 52 in the interior of the semipermeable body 32. Together, the predetermined wall width w and the predetermined plug thickness t define an "effective thickness" L of the semipermeable body. As described below, by varying the effective thickness L of the semipermeable body, the liquid permeation rate through the body can be controlled; this is beneficial because, for example, different desired liquid permeation rates through osmotic delivery system plugs 30 according to the present invention are obtainable from plugs formed from the same material having the same permeability coefficient and liquid uptake characteristics. This is further beneficial because biocompatibility and toxicity tests need only be performed on one semipermeable material.

Theoretically, the liquid permeation rate dV/dt through a semipermeable membrane sheet in an osmotic delivery system is equal to the liquid permeability coefficient P for the membrane multiplied by the surface area of the membrane A and the osmotic pressure difference $\Delta\pi$ between the osmotic agent and the liquid on the other side of the membrane, divided by the thickness of the membrane sheet L.

$$dV/dt = PA\Delta\pi/L$$

The beneficial agent delivery rate dMt/dt is theoretically equal to the liquid permeation rate dV/dt multiplied by the concentration C of the beneficial agent.

$$dMt/dt = dV/dt \cdot C = \{PA\Delta\pi/L\} \cdot C$$

If the surface area A of the membrane body is kept constant, then for a selected membrane material, osmotic agent, and beneficial agent concentration, the liquid permeation rate dV/dt through the membrane and the beneficial agent delivery rate dMt/dt are each theoretically inversely proportional to the thickness L of the membrane.

Thus, by varying the thickness L of a membrane sheet, for example, the liquid permeation rate may be controlled. The present invention controls the liquid permeation rate dV/dt through the membrane plug 30 by varying the effective thickness L of the semipermeable plug body 32, which corresponds to the theoretical thickness L of a typical sheet membrane, for example. Thus, by varying the size of the recess or hollow interior portion 52, or, in other words, by varying the predetermined plug thickness t and/or the predetermined wall width w, the effective thickness L of the semipermeable body 32 of the osmotic delivery system plug 30 may also be varied. For instance, by increasing the effective thickness L of the semipermeable body 32 of the plug 30, the liquid permeation rate dV/dt through the plug may be decreased. Although the plug thickness t primarily influences the liquid permeation rate through the membrane plug 30 (see FIGS. 8–11), the wall width w also affects the liquid permeation rate, but to a lesser extent than the plug thickness t. The influence of the wall width w on the liquid permeation rate through the semipermeable membrane body 32 may be easily determined through experimentation.

In the above described manner, the liquid permeation rate dV/dt through the membrane plug 30 can be controlled. This is advantageous because low liquid uptake membrane materials can be used to fashion osmotic delivery system plugs 30 according to the present invention with fast liquid permeation rates. Such fast permeation rates were previously achieved by fashioning plugs out of high liquid uptake and possibly biologically unstable membrane materials, which occasionally permit items in the interior of the osmotic delivery system to leak to the environment of use.

Osmotic delivery system plugs 30 according to the present invention permit the administration of beneficial agents 72 from osmotic delivery systems at rapid delivery rates over a relatively short period of time, even though the plugs may use a semipermeable material which, as measured against previous membrane plugs, has a low permeability coefficient. These low permeability coefficient membrane materials do not have high liquid uptake characteristics, and do not swell as dramatically as high uptake materials when the liquid from the surrounding environment permeates through the membrane. Thus, the osmotic delivery plug 30, that includes a hollow interior portion 52 sized for a fast liquid permeation rate, does not overly swell and creep out of the capsule, or permit the osmotic agent 78 to leak from the capsule. Furthermore, the osmotic delivery plug 30 may be made from materials that are stable in biological environments, and do not significantly degrade over time, which could permit fluids, crystals, or powder within the interior of the capsule 71 to leak to the environment of use.

Because the present invention permits high liquid permeation rates to be obtained from plugs 30 made from generally low uptake materials which can fit tightly into the osmotic delivery system enclosure, the plug remains structurally rigid, and there is no need for glues or adhesives, typically necessary to keep high uptake and swelling membrane plugs intact.

Another important benefit of controlling the effective thickness L of the osmotic delivery system plug 30 is that different liquid permeation rates are obtainable from the same semipermeable material having a set permeability coefficient. A different membrane material need not be used for every system which has a different desired beneficial agent delivery rate, and biocompatibility and toxicity tests need only be performed on one semipermeable material.

Figure 4B:
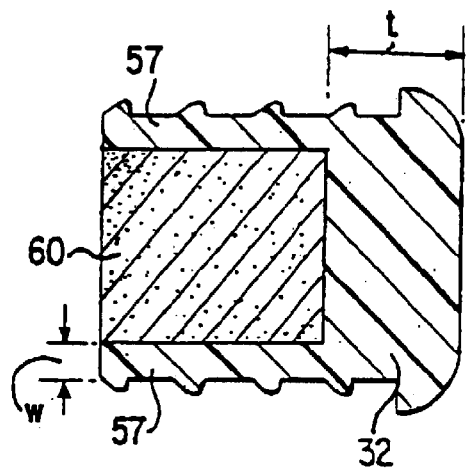
FIG. 4B is a sectional view of an osmotic delivery system plug, which includes an insert, according to the present invention taken along the line 4—4 of FIG. 3.

The hollow interior portion or recess 52 illustrated in FIGS. 4A and 4B is cylindrical, having a recess diameter 46. By increasing the recess diameter 46, the predetermined wall width w decreases. Although the cylindrical configuration of the recess 52 is preferred, other configuration recesses fall within the confines of the present invention. For example, the recess or hollow interior portion 52 may be square, rectangular, octagonal, triangular, oval, half circular, or circular. Likewise, the hollow interior portion 52 may be a series or plurality of recesses, tubes, slots, or gaps within the interior of the semipermeable body 32. All of the above, and other configurations, would function to control the effective thickness L of the semipermeable body 32 as contemplated by the present invention.

The semipermeable body 32 is preferably injection molded. However, the semipermeable body may be fashioned by a different process. For example, the semipermeable body may also be made from extrusion, reaction injection molding, rotational molding, thermoforming, compression molding, and other known casting processes. Injection molding is preferable in that the ejector pin or core may be used to form the recess 52, and different length and sized ejector pins or cores may be easily changed to fashion different sized recesses to controllably vary the liquid permeation rate through the membrane body 32 of the plug 30. Additionally, the recess 52 may be formed in the semipermeable body 32 after the semipermeable body 32 has been formed without a recess. For example, a cylinder of semipermeable material may be fabricated and sliced into smaller cylinders. Thereafter, a cylindrical section may be removed from the semipermeable body to form the recess 52 in the body. Thus, the liquid permeation rate through the semipermeable body 32 may be changed by first making a semipermeable body having a liquid permeability coefficient and a thickness, and then changing the thickness of the semipermeable body to alter the liquid permeation rate through the semipermeable body.

In one embodiment of the present invention, the semipermeable body 32 was formed by injection molding. The semipermeable material used in the injection molding process was TECOPHILIC HP60D-20. The following injection molding operating parameters were used to form the above described semipermeable body:

| | | | |
|---|---|---|---|
| NOZZLE TEMP. ZONE 1 | 183° C. | INJ. TIME | 4 SEC. |
| BARREL TEMP. ZONE 2 | 180° C. | HOLD TIME | 2 SEC. |
| BARREL TEMP. ZONE 3 | 175° C. | CLAMP CLOSED TIME | 20 SEC. |
| BARREL TEMP. ZONE 4 | 170° C. | SCREW SPEED | 430 RPM |
| HOLDING PRESSURE | 500 PSI | BACK PRESSURE | 200 PSI |
| INJECTION PRESSURE | 500 PSI | | |

Figure 5:
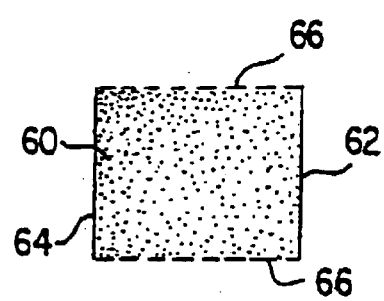
FIG. 5 is a side view of an insert of an osmotic delivery system plug according to the present invention.

FIGS. 5 and 6 illustrate an insert 60 which is included in an exemplary osmotic delivery plug 30 or osmotic delivery system semipermeable body assembly in accordance with the present invention. As shown in FIG. 4B, the insert 60 is intended for insertion into the cylindrical recess or hollow interior portion 52. In the embodiment of the present invention illustrated in FIGS. 5 and 6, the insert is cylindrically shaped to match the shape of the hollow interior portion 52. Thus configured, the insert 60 has a cylindrical peripheral surface 66, a flat top surface 62, and flat contact surface 64 located opposite the top surface. The insert 60 is sized such that the hollow interior portion 52 matingly receives the insert. In instances where the effective thickness L of the membrane body 32 is decreased by increasing the recess diameter 46 of the hollow interior portion 52, the diameter of the insert 60 is also increased to substantially match the increased recess diameter 46. Likewise, the longitudinal length of the insert 60 depicted in FIGS. 5 and 6 is substantially equal to the depth of the recess 52 within the semipermeable body 32.

It will be appreciated that the insert 60 may be in any number of different shapes and sizes, but preferably matches the shape and size of the hollow interior portion 52 into which the insert 60 is inserted.

The insert 60 is preferably inserted in the recess 52 for assisting the semipermeable body 32 in effecting a seal with the interior of the enclosure 71. Because the semipermeable body 32 is typically flexible and resilient, the wall 57 may flex toward the interior of the recess 52 after the plug 30 is inserted into the enclosure 71. By inserting the preferably rigid insert 60 into the insert opening 55 of the recess 52 such that the insert is matingly received, the wall 57 will not flex inwardly toward the insert and the seal formed by the outer surface 38 and the ribs 34 is maintained.

It is also preferable that the insert 60 be substantially pervious to liquids, permitting the liquid which has permeated through the semipermeable body 32 to freely travel through the insert to the osmotic agent 78 of the osmotic delivery system 70. It is preferable that the insert 60 be more pervious to liquids than the semipermeable membrane body 32 such that the liquid permeation rate through the semipermeable body 32 with the insert 60 therein is not substantially affected by the liquid permeability of the insert. In other words, the liquid permeation rate through the semipermeable body 32 should not change significantly because the insert 60 has been inserted into the recess 52. Because the insert 60 is preferably more pervious to liquids than the semipermeable body 32, the insert 60 will not adversely affect the liquid permeation rate through the semipermeable body 32 to any significant degree. Materials from which the insert 60 may be fashioned include, but are not limited to, metals, glasses, and plastics which are fashioned with pores, holes or liquid channels. Preferred materials for the insert 60 are fritted glass or metal, and macroporous polymers.

Because the insert 60 according to the present invention maintains the seal of the semipermeable body 32 with the enclosure 71, there is no need for glues or adhesives to effect a seal.

Alternatively, the insert 60 may not be inserted into the recess 52. Although the insert 60 is preferred because it maintains the seal, instances may arise where the insert 60 is not necessary. For example, if the semipermeable body 32, according to an alternative embodiment of the present invention (not depicted), has a hollow interior portion 52 with a small recess diameter 46 and predetermined depth, the insert 60 may not be needed to assist in effecting the seal. Generally, the predetermined wall thickness w and the structural characteristics of the semipermeable body 32 determine whether or not a rigid insert is needed to assist in effecting the seal, which is capable of being determined by experimental methods well known in the art.

The insert 60 may also be impervious to liquids or partially impervious to some liquids such that the liquid permeation rate through the osmotic delivery system plug 30 is altered by the insert material and its configuration. For example, the insert may be fashioned from a semipermeable material having a different permeability coefficient than that of the semipermeable body 32.

The insert 60 may also function as an osmotic agent. For example, the insert may be fashioned from polymers blended with 60% sodium chloride or salt embedded in a rigid structure. In such an embodiment, the sodium chloride will function as an "initial" osmotic engine, helping initiate the flow of beneficial agent from the osmotic delivery system 70 upon insertion into a liquid environment of use. After the sodium chloride has lost its osmotic abilities and/or has dissolved away, the polymer (having pores, for example) remains in the recess 52 and assists in making the seal and/or also partially controlling the permeation rate of liquid into the enclosure 71.

FIG. 7 illustrates an example of an osmotic delivery device or system 70 according to the present invention. The configuration illustrated in FIG. 7 is one example of an osmotic delivery device and is not to be construed as limiting the present invention. The present invention is generally applicable to all osmotic delivery devices having any number of shapes, and to all such devices administered in any variety of methods such as oral, ruminal, and implantable osmotic delivery techniques. Such devices may also be placed in reservoirs, tanks, or pools.

The osmotic drug delivery system 70, as illustrated in FIG. 7, includes an elongated substantially cylindrical enclosure 71 having an opening 79 which, as illustrated in FIG. 7, is plugged with the plug 30. The end of the enclosure opposite the opening 79 has one or more delivery ports 75 for delivering a beneficial agent 72 from the osmotic delivery system 70. The elongated enclosure 71 is formed of a material which is sufficiently rigid to withstand expansion of an osmotic agent 78 without changing size or shape. The enclosure 71 is preferably substantially impermeable to fluids in the environment as well as to ingredients contained within the osmotic delivery device such that the migration of such materials into or out of the device through the impermeable material of the enclosure is so low as to have substantially no adverse impact on the function of the osmotic delivery device.

Within the enclosure 71 is a beneficial agent 72 to be delivered. Such a beneficial agent 72 may optionally include pharmaceutically acceptable carriers and/or additional ingredients such as antioxidants, stabilizing agents, permeation enhancers, etc.

The embodiment of the present invention illustrated in FIG. 7 includes an optional movable separating member or movable piston 74. The osmotic agent 78 within the enclosure 71 is separated from the beneficial agent 72 by the movable piston 74. The enclosure 71 receives the osmotic agent 78, which in the embodiment of the present invention depicted in FIG. 7 is one or more osmotic tablets. Osmotic agents 78, specifically the osmotic tablet of the embodiment of the present invention illustrated in FIG. 7, drive the osmotic flow of osmotic delivery devices. However, the osmotic agent 78 need not be a tablet; it may be other conceivable shapes, textures, densities, and consistencies and still be within the confines of the present invention.

When used, the movable separating member or movable piston 74 is a substantially cylindrical member which is configured to fit within the enclosure 71 in a sealed manner which allows the piston to slide along a longitudinal direction within the enclosure. The piston 74 preferably is formed of an impermeable resilient material and includes annular ring shape protrusions 76 which form a movable or sliding seal with the inner surface of the enclosure.

As illustrated in FIG. 7, the osmotic delivery device 70 includes the above-described osmotic delivery system plug 30, which is inserted in the opening 79 of the enclosure 71 after placing the osmotic agent 78 within the enclosure. The plug 30 allows liquid to pass from an environment of use into the enclosure 71 to cause the osmotic agent 78 to swell. However, as described above, the material forming the semipermeable body 32 is largely impermeable to the materials within the enclosure and other ingredients within the environment of use.

Materials which may be used for the enclosure 71 must be sufficiently strong to ensure that the enclosure will not leak, crack, break, or distort under stresses to which it would be subjected during implantation or under stresses due to the pressures generated during operation. Because the osmotic delivery system plug 30 enables rapid liquid permeation rates to be obtained from a semipermeable body 32 made from a low uptake membrane material, the risk that the enclosure 71 may rupture or crack from pressures generated by high uptake and high swelling membrane plugs is reduced.

The enclosure 71 may be formed of chemically inert and biocompatible, natural or synthetic materials which are known in the art. The enclosure material is preferably a non-bioerodible material which may remain in the patient after use, such as titanium or a titanium alloy, and is largely impermeable to materials within and outside the enclosure. However, the material of the enclosure may alternatively be a bioerodible material which bioerodes in the environment after dispensing the beneficial agent. Generally, preferred materials for the enclosure 71 are those acceptable for human implants.

In general, typical materials of construction suitable for the enclosure 71 according to the present invention include nonreactive polymers or biocompatible metals or alloys. The polymers include acrylonitrile polymers such as acrylonitrile-butadiene-styrene terpolymer, and the like; halogenated polymers such as polytetrafluoroethylene, polychlorotrifluoroethylene copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the enclosure 71 include stainless steel, titanium, platinum, tantalum, gold, and their alloys, as well as gold-plated ferrous alloys, platinum-plated ferrous alloys, cobalt-chromium alloys and titanium nitride coated stainless steel.

In general, materials suitable for use in the movable separating member 74 are elastomeric materials including the nonreactive polymers listed above, as well as elastomers in general, such as polyurethanes and polyamides, chlorinated rubbers, styrene-butadiene rubbers, and chloroprene rubbers.

The osmotic agent 78, illustrated in FIG. 7 by an osmotic tablet, is a liquid-attracting agent used to drive the flow of the beneficial agent. The osmotic agent may be an osmagent, an osmopolymer, or a mixture of the two. Species which fall within the category of osmagent, i.e., the nonvolatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or may be synthetic, and examples of osmopolymers are well known in the art. Examples include: poly(hydroxy-alkyl methacrylates) with a molecular weight of 30,000 to 5,000,000, poly(vinylpyrrolidone) with a molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite® polyacrylic acids having molecular weights of 80,000 to 200,000, Polyox Polyethylene oxide polymers having molecular weights of 100,000 to 5,000,000, starch graft copolymers, and Aqua-Keeps® acrylate polymer polysaccharides.

The osmotic agent 78 may be manufactured by a variety of techniques, many of which are known in the art. In one such technique, an active osmotic agent 78 is prepared as solid or semisolid formulations and pressed into pellets or tablets whose dimensions correspond to slightly less than the internal dimensions of the respective chambers which they will occupy in the enclosure interior. Depending on the nature of the materials used, the agent and other solid ingredients which may be included may be processed prior to the formation of the pellets by such procedures as ballmilling, calendaring, stirring or rollmilling to achieve a fine particle size and hence fairly uniform mixtures of each. The enclosure 71 may be formed from any of the wall-forming materials disclosed above by the use of a mold, with the materials applied either over the mold or inside the mold, depending on the mold configuration. Any of the wide variety of techniques known in the pharmaceutical industry may be used to form the enclosure 71.

In assembling the osmotic delivery device 70 according to one embodiment of the present invention, the piston 74 is first inserted into the enclosure 71. Once the osmotic agent 78, in the form of pellets or tablets, has been formed, it is placed inside the preformed enclosure 71 on top of the separating member 74. Then the osmotic delivery system plug 30, according to one embodiment of the present invention, is placed into the opening 79 of the enclosure 71 to close off and seal one end of the osmotic delivery system.

The delivery port 75 is an orifice formed by conventional techniques which are known in the art. Included among these methods are mechanical drilling, laser drilling, and molding. The enclosure will contain at least one such delivery port 75, and in most configurations, one delivery port will suffice. However, two or more delivery ports 75 may be present without departing from the present invention. The delivery port 75 may also be formed in a separate plug-like device and then inserted into a second opening (not illustrated) of the enclosure 71 opposite the first opening 79. The dimensions of the port 75 in terms of both diameter and length will vary with the type of beneficial agent 72, the rate at which the beneficial agent is to be delivered, and the environment into which it is to be delivered. The considerations involved in determining the optimum dimensions of the delivery port 75 for any particular enclosure or beneficial agent 72 are the same as those for delivery ports or orifices of enclosures of the prior art, and selection of the appropriate dimensions will be readily apparent to those skilled in the art.

In other embodiments of this invention, the beneficial agent 72 contained in the enclosure 71 may include flowable compositions such as liquids, suspension, or slurries, which are typically poured into the enclosure after the osmotic agent 78 and the piston 74 have been inserted.

Animals to whom beneficial agents may be administered using systems of this invention include humans and other animals. The invention is of particular interest for application to humans and household, sport, and farm animals, particularly mammals. For the administration of beneficial agents to animals, the devices of the present invention may be implanted subcutaneously or intraperitoneally wherein aqueous body fluids or liquids are available to activate the osmotic agent. Devices of the invention may also be administered to the rumen of ruminant animals, in which embodiment the devices may further comprise a density element for maintaining the device in the rumen for extended periods of time of up to 120 days or longer. Density elements are well known in the art of drug delivery devices.

The present invention applies to the administration of beneficial agents in general, which include any physiologically or pharmacologically active substance. The beneficial agent 72 may be any of the agents which are known to be delivered to the body of a human or an animal such as medicaments, vitamins, nutrients, or the like. The beneficial agent 72 may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandin fertility promoters, growth factors, coagulation factors, human pancreas hormone releasing factor, analogs and derivatives of these compounds, and pharmaceutically acceptable salts of these compounds, or their analogs or derivatives.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, acetate, sulfate, laurylate, oleate, and salicylate. For acidic compounds, salts of metals, amines or organic cations may be used. Derivatives such as esters, ethers and amides can also be used. A beneficial agent can be used alone or mixed with other agents.

According to other embodiments of the present invention, the enclosure 71 may take different forms. For example, as described above, the delivery port 75 may be formed in a soft impermeable material inserted into the enclosure 71. In addition, the movable separating member 74 may be a flexible member such as a diaphragm, partition, pad, flat sheet, spheroid, or rigid metal alloy, and may be made of any number of inert materials. Furthermore, the osmotic device 70 may function without the separating member 74, having simply an interface between the osmotic agent 78 and the beneficial agent 72.

The devices of this invention are also useful in environments outside of physiological or aqueous environments. For example, the devices may be used in intravenous systems (attached to an IV pump or bag or to an IV bottle, for example) for delivering beneficial agents to an animal, primarily to humans. They may also be utilized in blood oxygenators, kidney dialysis and electrophoresis, for example. Additionally, devices of the present invention may be used in the biotechnology area, such as to deliver nutrients or growth regulating compounds to cell cultures. In such instances, activating mechanisms such as mechanical mechanisms are particularly useful.

Figure 1:
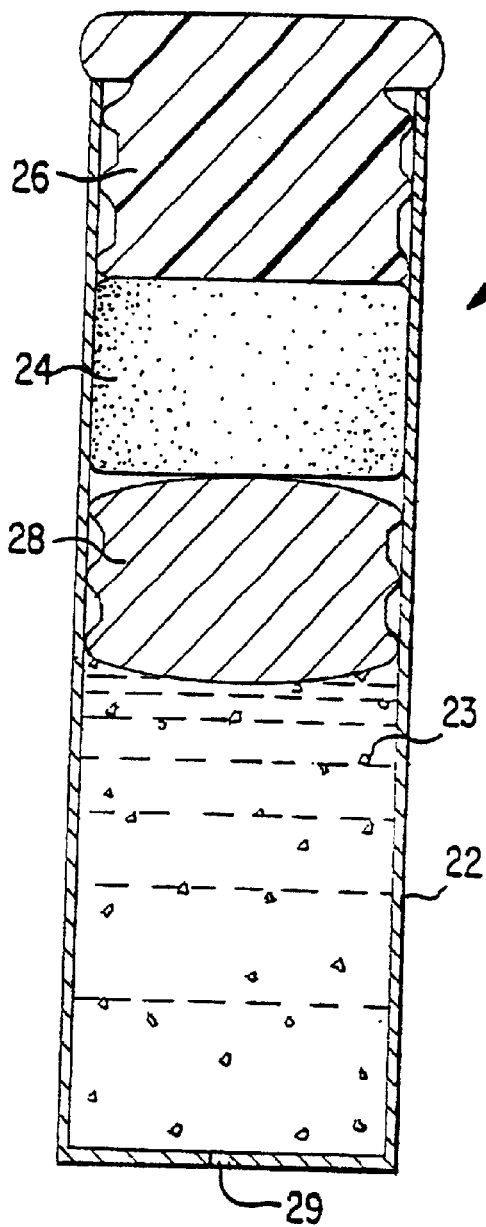
FIG. 1 is a cross-sectional view of a prior art osmotic drug delivery device which incorporates a membrane plug.
Figure 8:
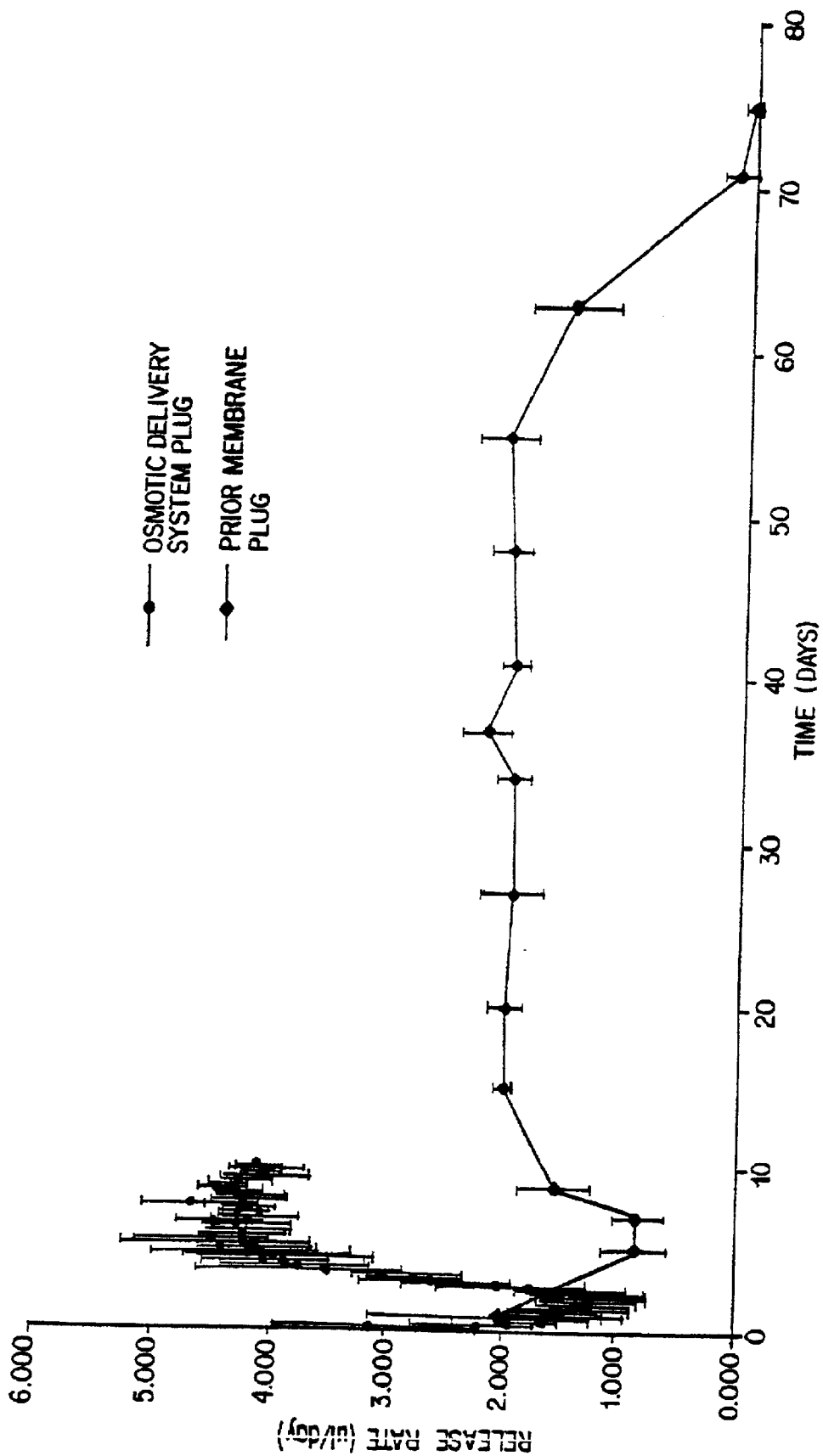
FIG. 8 is a graph illustrating the increased release rate of an osmotic delivery system according to the present invention, which utilizes an osmotic delivery system plug according to the present invention.

FIG. 8 is a graph of the release rate of beneficial agent over time and compares an osmotic delivery system according to the present invention with an osmotic delivery system incorporating a conventional membrane plug, such as that illustrated in FIG. 1. As described above, the osmotic delivery system 70, according to the present invention, includes an osmotic delivery system plug 30, according to the present invention. Both the prior membrane plug and the osmotic delivery system plug 30 tested in FIG. 8 were made of the same membrane material, PEBAX. The chemical structure of PEBAX is:

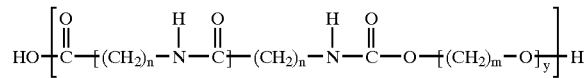

wherein, n=5, or 11 m=2, or 4 x and y are selected according to the desired molecular weight.

As shown in FIG. 8, the osmotic delivery system 70 incorporating the prior membrane plug delivered approximately 2 μl/day of the beneficial agent from the osmotic delivery system. Comparatively, the osmotic delivery system having a membrane plug 30 according to the present invention released about 4 μl/day of beneficial agent even though the same semipermeable material was used for the plugs in each osmotic delivery system tested.

Figure 9:
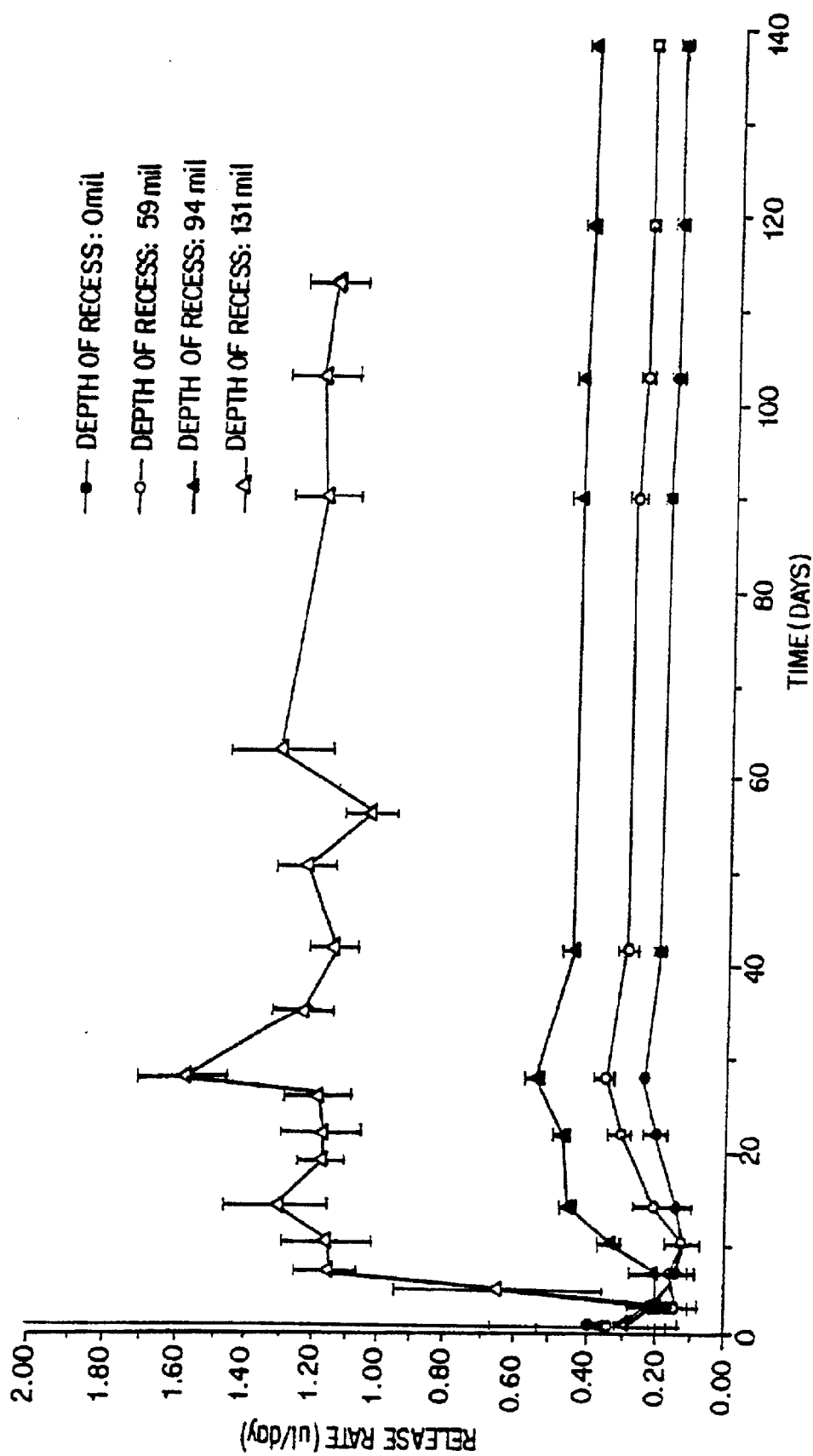
FIG. 9 is a graph illustrating the release rate of osmotic delivery systems according to the present invention having osmotic delivery system plugs according to the present invention; the plugs have different depth recesses and are all made from a polyurethane material with 18% water uptake.
Figure 10:
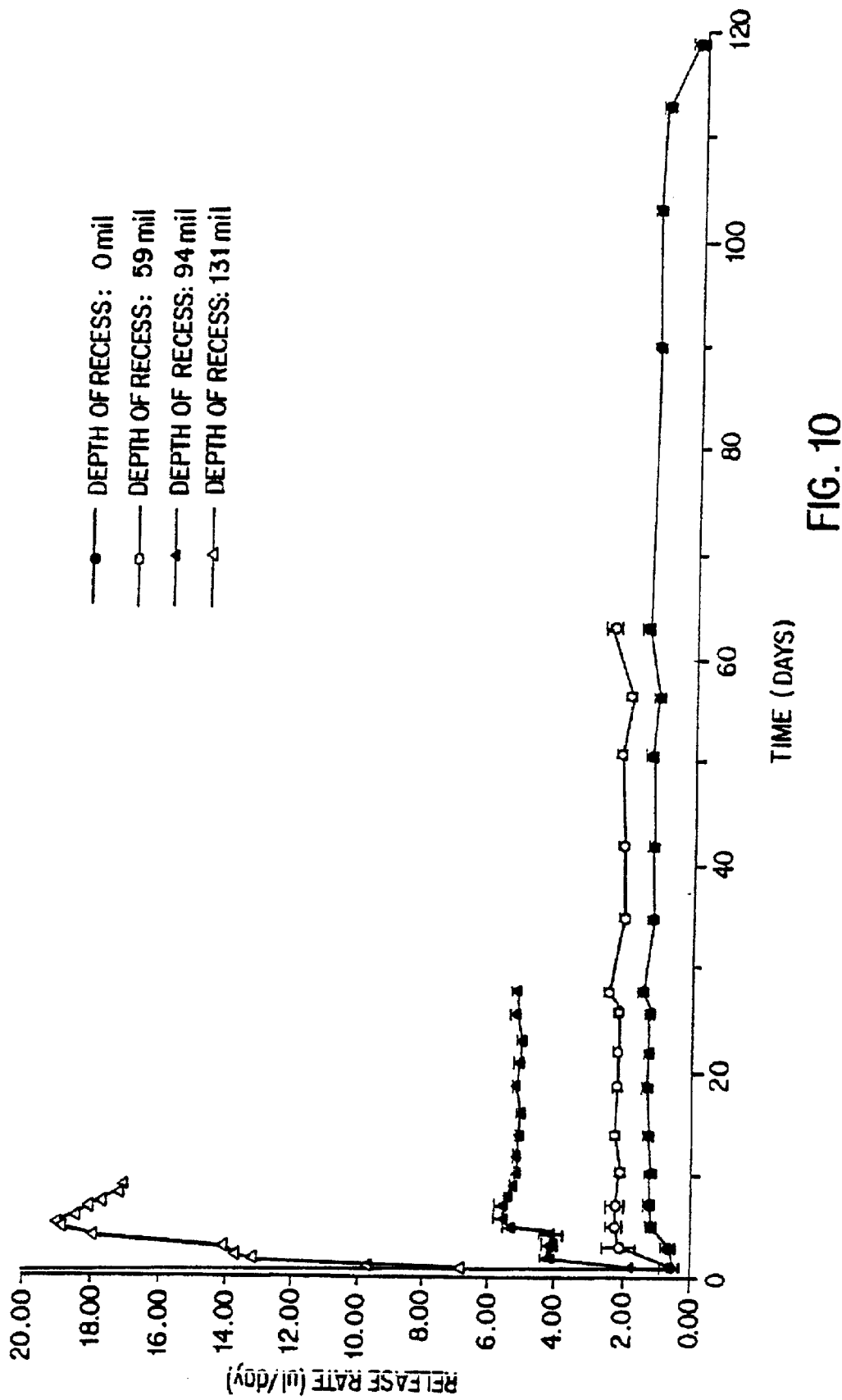
FIG. 10 is a graph illustrating the release rate of osmotic delivery systems according to the present invention having osmotic delivery system plugs according to the present invention; the plugs have different depth recesses and are all made from a polyurethane material with 33% water uptake.
Figure 11:
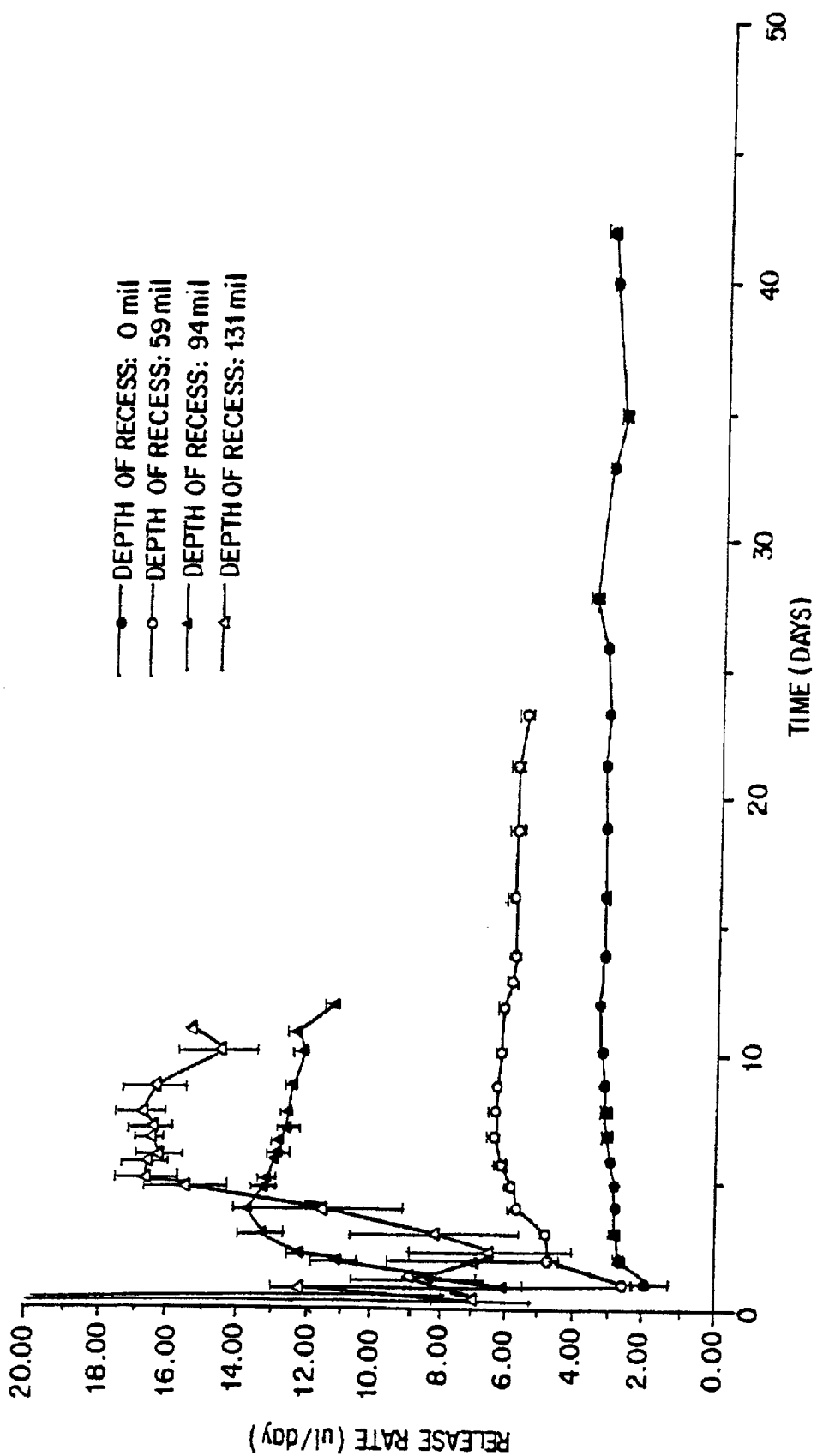
FIG. 11 is a graph illustrating the release rate of osmotic delivery systems according to the present invention having osmotic delivery system plugs according to the present invention; the plugs have different depth recesses and are all made from a polyurethane material with 49% water uptake.

FIGS. 9–11 are also graphs of the release rate of beneficial agent over time and each compare osmotic delivery systems according to the present invention having membrane plugs 30 with various recesses 52.

The objectives of the experiments conducted to obtain the results depicted in FIGS. 9–11 were to evaluate (1) the influence of the depth of the interior portion 52 of the membrane plug 30 on the release rate of beneficial agent, and (2) the influence of the water uptake of membrane plug materials on the release rate. The subassembly components of the osmotic delivery systems 70 tested included: titanium enclosures 71; 80% sodium chloride osmotic agent 78 (2×50 mg); C-flex pistons 74; silicone medical fluid (350 cs); and HDPE spiral orifice delivery ports (6 mil channel diameter). Spiral orifice delivery ports are disclosed in U.S. patent Ser. No. 08/595,761, the entire disclosure of which is incorporated herein by reference.

The vehicle formulation of the beneficial agent used in the osmotic delivery systems tested was 2% Blue #1 in purified water (USP). The configuration of the membrane plugs 30 were: HP-60D-20b (1.5% clearance) with recess depths of 0, 59, 94 and 133 mils; HP-60D-42 (7.5% clearance) with recess depths of 0, 59, 94 and 133 mils; and HP-60D-60 (7.5% clearance) with recess depths of 0, 59, 94 and 133 mils. The inserts 60 tested in the membrane plugs 30 were made from HDPE porous rods with a pore size of 15–45μ (available from POREX).

All pistons and enclosures were prelubricated. Sequentially, pistons 74 were first inserted into the enclosures 71. The enclosures were then filled with 10 μl of PEG-400 and thereafter, two osmotic agent 78 tablets were inserted. The HDPE insert plug 30 was presoaked in PEG-400 to eliminate any air trapped in the pores. The semipermeable bodies 32 were ultradried and the porous HDPE inserts were preinserted into the recess 52. After the osmotic delivery systems were assembled, they were then submerged in a water bath at 37° C. Beneficial agent release rate measurements were determined three times during the first week after insertion, two times during the second week, and weekly thereafter. The depth of the recess 52 and corresponding length of the insert 60 were either 0, 59, 94, or 131 mils, as measured from the insert ends 56 of the membrane plugs 30. The diameter of the inserts 60 and recesses 52 for all tests was kept constant and was approximately 2.0 mm. The diameter and thickness or length (measured from end to end) of the semipermeable bodies 32 were also kept constant and were approximately 2.99 mm (diameter) and 150 mils (length). The specific membrane material used in the experiments was Tecophilic polyurethane (TECOPHILIC®, commercially available from THERMEDICS) having either 18%, 33% or 49% water uptake. The chemical structure of Tecophilic polyurethane is understood to be:

Where the values of x and y depend on the monomer composition of the polymer and determine the water uptake value, the values of a and b depend on the monomer distribution of the polymer, m=20–25, and n=12–17.

The test results are summarized below in Table 1.

TABLE 1

Summary of beneficial agent release rate tests for osmotic delivery system plugs having different depth recesses.

| Membrane | Water uptake (%) | Thickness t (mil) | Depth of hollow (mil) | Release rate (μl/day) | Duration (days) |
|---|---|---|---|---|---|
| Teco72b (#18709) | 18 | 151 | 0 | 0.205 | 700 |
| Teco72b (#20536) | 18 | 92 | 59 | 0.298 | 490 |
| Teco72b (#19305) | 18 | 57 | 94 | 0.468 | 310 |
| Teco72b (#20535) | 18 | 20 | 131 | 1.218 | 120 |
| Teco77 (#18710) | 33 | 151 | 0 | 1.322 | 110 |
| Teco77 (#20509) | 33 | 92 | 59 | 2.226 | 65 |
| Teco77 (#20452) | 33 | 57 | 94 | 5.086 | 29 |
| Teco77 (#20508) | 33 | 20 | 131 | 18.138 | 8 |
| Teco73 (#18710) | 49 | 151 | 0 | 3.188 | 46 |
| Teco73 (#20509) | 49 | 92 | 59 | 5.897 | 25 |
| Teco73 (#20452) | 49 | 57 | 94 | 12.568 | 12 |
| Teco73 (#20508) | 49 | 20 | 131 | 16.121 | 9 |

The test results are illustrated in FIGS. 9–11. As described above, FIGS. 9–11 illustrate the release rate over time for osmotic delivery systems including TECOPHILIC® membrane plugs 30 having constant water uptake and different depth recesses 52. As illustrated, by increasing the depth of recess 52 (controlling the effective thickness L of the membrane plugs), the release rate of the beneficial agent increases. Thus, the liquid permeation rate through the membrane plugs 30 according to the present invention may be controlled even though the permeability coefficient for the membrane material is constant. In sum, many different membrane plugs 30 (having different effective thicknesses L and different permeation rates) may be formed from one membrane material. This is especially advantageous in that delivery system plugs, according to the present invention, may be manufactured from one semipermeable material, which has been tested and shown to be biocompatible, does not have high uptake characteristics, does not tend to dislodge from the delivery system enclosure, and does not permit items within the osmotic delivery system to escape or leak to the environment of use.

FIGS. 13–20, 25, and 28 illustrate alternative embodiments of osmotic delivery systems according to the present invention. The foregoing and following discussion of the

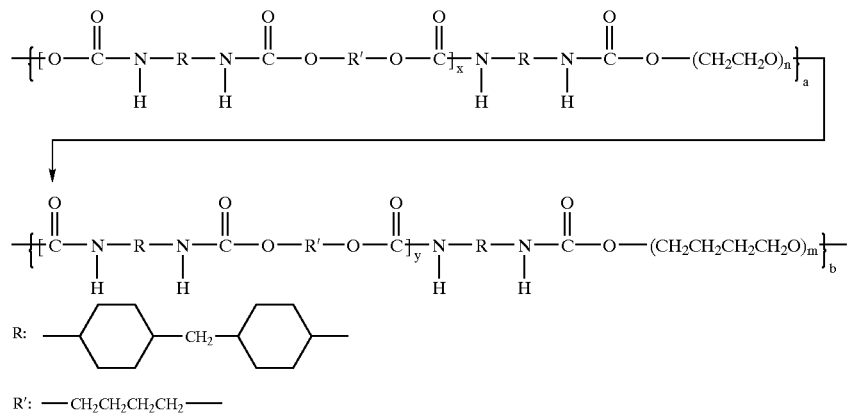

benefits and functions of the osmotic delivery system 70 also applies to the osmotic delivery systems 270, 370, 470, 570, 670, 770, 870, 970, 1070, and 2070. Thus, the osmotic delivery systems illustrated in FIGS. 13–20, 25, and 28 have been assigned corresponding reference numbers as the osmotic delivery system 70, increased by hundreds. The osmotic delivery systems illustrated in FIGS. 13–20, 25, and 28 also include many additional features and inherent functions, as described further below.

Figure 13:
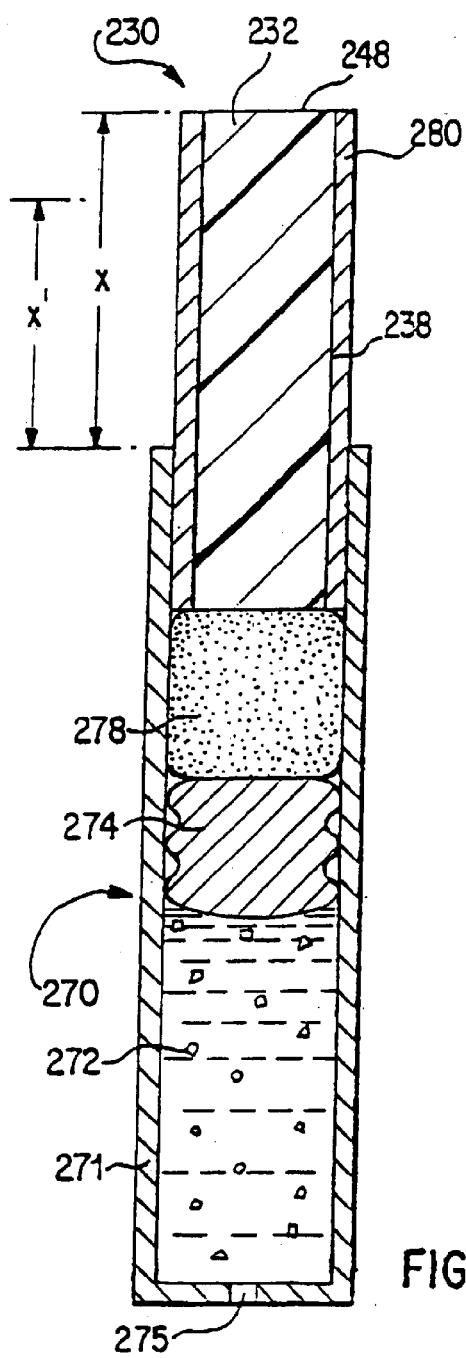
FIG. 13 is a sectional view of another osmotic delivery system according to the present invention having a semipermeable body and liquid impermeable sleeve, where both the semipermeable body and the liquid impermeable sleeve have been inserted in an opening of the enclosure of the osmotic delivery system.

FIG. 13 illustrates one embodiment of an osmotic delivery device or system 270. As illustrated in FIG. 13, the osmotic delivery system 270 includes an elongated substantially cylindrical enclosure 271 having an opening through which a semipermeable body assembly 230 has been inserted. The semipermeable body assembly 230 includes a semipermeable body 232 and a liquid impermeable sleeve 280. The end of the enclosure 271 opposite the opening through which the semipermeable body assembly 230 has been inserted has one or more delivery ports 275 for delivering a beneficial agent 272 from the osmotic delivery system 270. The elongated enclosure 271 is formed of a material which is sufficiently rigid to withstand expansion of an osmotic agent 278 without changing shape or size. The elongated enclosure 271 is preferably substantially impermeable to fluids in the environment of use as well as to ingredients contained within the osmotic delivery system 270 such that the migration of such materials into or out of the device through the impermeable material of the enclosure is so low as to have substantially no adverse impact on the function of the osmotic delivery device.

Within the enclosure 271 is the beneficial agent 272 to be delivered, and an optional piston 274. The osmotic agent 278 within the enclosure 271 is separated from the beneficial agent 272 by the piston 274. The enclosure 271 receives the osmotic agent 278, which in the embodiment of the present invention depicted in FIG. 13 is one or more osmotic tablets. The osmotic agent 278, in the form of a tablet, drives the osmotic flow of the osmotic delivery system 270.

As illustrated in FIG. 13, the osmotic delivery system 270 includes an osmotic delivery system semipermeable body assembly 230 having the semipermeable body 232 and the liquid impermeable sleeve 280 which have been inserted into the cylindrical opening of the enclosure 271. The osmotic agent 278 is directly adjacent to or touching the semipermeable body 232. The semipermeable body 232 allows liquid to pass from an environment of use into the enclosure 271 to cause the osmotic agent 278 to swell. However, as described earlier, the material forming the semipermeable body 232 is largely impermeable to the materials within the enclosure and other ingredients within the environment of use. The semipermeable body 232 and the liquid impermeable sleeve 280 together define the osmotic delivery system semipermeable body assembly 230 that controls the delivery rate of the beneficial agent 272 from the osmotic delivery system 270. The configuration of the semipermeable body 232 and the liquid impermeable sleeve 280 dictates the liquid permeation rate through the semipermeable body 252, which generally controls the delivery rate of the beneficial agent 272 from the osmotic delivery system 270.

The semipermeable body 232 is cylindrically shaped, and the outer or exterior cylindrical surface 238 of the semipermeable body 232 touches or contacts the sleeve 280. The liquid impermeable sleeve 280 is tubular or barrel shaped, although it may be shaped otherwise and still be within the confines of the present invention. For example, the liquid impermeable sleeve 280 may be thimble-shaped, V-shaped, or C-shaped. The interior cylindrical surface of the liquid impermeable sleeve 280 abuts against the exterior cylindrical surface 238 of the semipermeable body 232. Thus, the liquid impermeable sleeve 280 forms a cylindrical tube surrounding the semipermeable body 232. In the embodiment of the present invention illustrated in FIG. 13, the liquid impermeable sleeve 280 is the same length as the semipermeable body 232 in the longitudinal direction of the semipermeable body, and the entire exterior cylindrical surface 238 of the semipermeable body abuts against the entire interior surface of the sleeve 280.

The liquid impermeable sleeve 280 is of the same material or a functionally similar material as that of the enclosure 271. The liquid impermeable sleeve 280 is formed from a material that is largely impermeable to the materials within the enclosure 271 and other ingredients within the environment of use. More specifically, the liquid impermeable sleeve 280 is preferably substantially impermeable to liquid in the environment of use as well as to ingredients contained with the osmotic delivery system 270 such that the migration of such materials into or out of the osmotic delivery system through the impermeable material of the liquid impermeable sleeve is so low as to have substantially no adverse impact on the function of the osmotic delivery device.

The liquid impermeable sleeve 280 and semipermeable body 232 are insertable into an opening of the osmotic delivery system enclosure 271. The exterior surface of the portion of the liquid impermeable sleeve 280 located within the enclosure 271 forms a seal with the interior surface of the enclosure 271. The portion of the exterior surface of the liquid impermeable sleeve 280 located within the enclosure 271 seals the interior of the enclosure 271 from the exterior environment. The seal may be enhanced by ribs on the exterior outer surface of the liquid impermeable sleeve 280 or the inner surface of the enclosure 271. Thus, the semipermeable body 232 and liquid impermeable sleeve 280, when inserted into the enclosure 271, together operate like a cork or stopper, obstructing and plugging the opening in the enclosure 271 of the osmotic delivery system 270. FIG. 13 illustrates the semipermeable body assembly 230 plugging the opening in the enclosure 271 of the osmotic delivery system 270.

The liquid impermeable sleeve 280 or the enclosure 271 may include other means to effect a seal between the liquid impermeable sleeve 280 and the enclosure 271, such as threads, a tight interference fit, grooves, ridges, lips, or other configurations which matingly join the liquid impermeable sleeve 280 with the enclosure 271 to prevent leakage. Additionally, an adhesive may be used to bond the liquid impermeable sleeve 280 to the enclosure 271. The semipermeable body 232 and the liquid impermeable sleeve 280 are, therefore, intended for at least partial insertion into opening of the enclosure 271. The seal formed between the semipermeable body assembly 230 and the enclosure 271 prevents liquid and other substances in the environment of use, besides the permeation liquid, from entering the osmotic delivery system 270 while also preventing materials from the inside of the delivery system from leaking or escaping to the environment of use.

Because the liquid impermeable sleeve 280 abuts against or contacts the entire exterior cylindrical surface 238 of the semipermeable body 232, the exterior cylindrical surface 238 of the semipermeable body is not immediately exposed to liquid when the osmotic delivery system 270 is located in the liquid environment of use. The liquid impermeable sleeve 280 may be fixed to the exterior cylindrical surface 238 of the semipermeable body 232 by an interference fit, an adhesive, or other means for attaching the liquid impermeable sleeve to the semipermeable body. The liquid impermeable sleeve 280 acts as a barrier or seal to prevent liquid from the environment of use from immediately and directly contacting the exterior cylindrical surface 238 of the semipermeable body 232 when the osmotic delivery system 270 is first exposed to liquid from the environment of use.

The liquid impermeable sleeve 280 is separate and distinct from the enclosure 271 (it is not integral with the enclosure), and surrounds only a portion of the entire peripheral surface (the exterior cylindrical surface 238 and end faces) of the semipermeable body 232 such that this surrounded portion of the peripheral surface is not immediately exposed to liquid when the osmotic delivery system is located in a liquid environment of use. As illustrated in FIG. 13, the liquid impermeable sleeve surrounds only the exterior cylindrical surface 238 of the semipermeable body 232 such that the exterior cylindrical surface 238 is not immediately exposed to liquid when the osmotic delivery system 270 is located in a liquid environment of use. When the osmotic delivery system 270 is inserted into a liquid environment of use, liquid does not immediately contact the entire exterior cylindrical surface 238 of the semipermeable body because it cannot traverse through the liquid impermeable sleeve 280 or immediately travel along the interior surface of the sleeve. Of course, after the permeation liquid has thoroughly soaked the semipermeable body 232, the entire exterior cylindrical surface 238 of the semipermeable body 232 will have contacted the liquid, but this will not occur immediately after the osmotic delivery system is inserted in the liquid environment of use. The liquid from the environment of use will only travel along the interior surface of the sleeve after the liquid has entirely permeated through the semipermeable body 232.

Because the liquid impermeable sleeve 280 does not abut against the entire peripheral surface of the semipermeable body 232, the semipermeable body 232 includes an exposure or liquid contact surface 248 defined by an area of the peripheral surface of the semipermeable body that is not in contact with or surrounded by the liquid impermeable sleeve 280. Thus, the exposure surface 248 is immediately exposed to liquids when the osmotic delivery system 270 is located in the liquid environment of use, while the outer or exterior cylindrical surface 238 is not immediately exposed to liquid when the osmotic delivery system is located in the liquid environment of use because the liquid impermeable sleeve 280 prevents the liquid from immediately contacting any surface of the semipermeable body 232 it is abutting. In other words, the permeation liquid may only travel through the semipermeable body 232 by first contacting the liquid contact surface 248, not the exterior cylindrical surface 238. Because the embodiment of the present invention illustrated in FIG. 13 includes a tubular liquid impermeable sleeve 280, the exposure surface 248 only includes that portion of the semipermeable body 232 that is incident to the exterior cylindrical surface 238. The exposure surface 248 is substantially perpendicular to the exterior cylindrical surface 238.

As described earlier, the beneficial delivery rate $dM_t/dt$ through a semipermeable body may be approximated by the following formula:

$$dM_t/dt = dV/dt \cdot C = \{PA \, \Delta\pi/L\} \cdot C$$

In the embodiments of the present invention illustrated in FIGS. 13–20, the liquid permeation rate through the semipermeable bodies 232, 332, 432, 532, 632, 732, 832, 932, 932', and 932" may be changed according to the above formula by varying the surface area of each semipermeable body that is exposed to liquid and/or the thickness of each of the semipermeable bodies 232, 332, 432, 532, 632, 732, 832, 932, 932', and 932".

As illustrated in FIG. 13, the semipermeable body 232 includes two opposing flat ends, one located within the enclosure 271, and the other located outside the enclosure and defining the exposure surface 248. Once the semipermeable body 232 and the liquid impermeable sleeve 280 surrounding the semipermeable body are inserted into the enclosure 271, the semipermeable body 232 is in liquid communication with the interior of the liquid impermeable enclosure 271 to permit liquid from the environment of use to permeate through the semipermeable body 232 to the osmotic agent 278 within the enclosure.

As described above in reference to the osmotic delivery system 70, the liquid permeation rate through the semipermeable body 32 may be controlled by varying the effective thickness L of the semipermeable body 32. In the embodiment of the present invention illustrated in FIG. 13, the liquid permeation rate through the semipermeable body 232 may be controlled or changed by varying the thickness of the semipermeable body 232. For example, by decreasing the thickness of the semipermeable body 232, the liquid permeation rate through the semipermeable body 232 will increase to correspondingly increase a delivery rate of the beneficial agent 272 from the osmotic delivery system 270. This may be achieved by first forming, such as by injection molding, the semipermeable body 232 from a semipermeable material having a predetermined liquid permeability coefficient. The semipermeable body 232 may also be formed with a set, or predetermined, longitudinal length or thickness that corresponds to a predetermined or desired liquid permeation rate. The semipermeable body 232 may also be formed with a predetermined diameter that defines a surface area of the liquid contact surface 248 and also corresponds to a predetermined or desired liquid permeation rate.

After the semipermeable body 232 has been formed, the liquid permeation rate through the semipermeable body 232 may be increased by decreasing the thickness of the semipermeable body. In the embodiment of the present invention illustrated in FIG. 13, the semipermeable body 232 surrounded by the liquid impermeable sleeve 280 may be cut to increase the liquid permeation rate through the semipermeable body, i.e., the thickness of the semipermeable body 232 is decreased to increase the liquid permeation rate through the semipermeable body 232. As illustrated in FIG. 13, the portion of the liquid impermeable sleeve 280 and semipermeable body 232 protruding from the enclosure 271 has a first length X, which may be decreased to a second length X' to increase the liquid permeation rate through the semipermeable body 232. The thickness or length of the semipermeable body 232 may be changed before or after the semipermeable body assembly 230 has been inserted into the opening of the enclosure 271. The exterior surface of the liquid impermeable sleeve 280 may include indicia spaced along the length of the sleeve that respectively indicate a location where the semipermeable body may be cut to achieve a desired liquid permeation rate or beneficial agent delivery rate.

The semipermeable body 232 and the sleeve 280 can be molded together such that the two items are "preassembled" and form the osmotic delivery system semipermeable assembly 230. For example, the liquid impermeable sleeve may be a laminate outer coating on the semipermeable body 232. The semipermeable body 232 can also be inserted into the sleeve 280 after it has been formed, in which case the sleeve 280 will matingly receive the semipermeable body 232. Accordingly, it should be realized that the length of the sleeve 280 and the semipermeable body 232 may be decreased separately and then assembled to form the semipermeable body assembly 230. Alternatively, the length of the semipermeable body assembly 230 (semipermeable body 232 and liquid impermeable sleeve 280) can be decreased by simultaneously decreasing the length of the semipermeable body and the liquid impermeable sleeve 280. Any variety of techniques may be used to decrease the thickness of the semipermeable body 232 and sleeve 280, including shearing, cutting, tearing, laser slicing, grinding, etc.

As described above, by varying the thickness of the semipermeable body 232, the liquid permeating rate through the body can be controlled. This is beneficial because, for example, different desired liquid permeation rates through the semipermeable body 232 are obtainable from semipermeable bodies 232 formed from the same material having the same permeability coefficient and liquid uptake characteristics. Thus, it is possible to obtain a multitude of different liquid permeation rates, and thus different beneficial agent delivery rates by simply decreasing the thickness of one preformed semipermeable body. This is further beneficial because biocompatability and toxicity tests need only be performed on one semipermeable material.

Because the exposure surface 248 defines the only surface area of the semipermeable membrane body 232 that is immediately exposed to liquids when the osmotic delivery system is located in its environment of use, the liquid permeation rate through the semipermeable body 232 may be easily increased by simply decreasing the length of the semipermeable body 232 and liquid impermeable sleeve 280. If the sleeve 280 and semipermeable body 232 are cut along a line perpendicular to the longitudinal axis of the sleeve and body, the exposure surface area will remain constant such that the increase in liquid permeation rate through the decreased length semipermeable assembly 230 may be easily estimated. Thus, an administrator of the osmotic delivery system 270 may change and estimate the permeation rate through the semipermeable body 230 to achieve a desired permeation rate by simply cutting or slicing one semipermeable body 232, rather than having to choose a different semipermeable body for each desired application.

The liquid permeation rate through the semipermeable body 232 may also be controlled or varied by removing a portion of the liquid impermeable sleeve 280 from the exterior cylindrical surface 238 of the semipermeable body to increase the amount of surface area of the semipermeable body 232 that is immediately exposed to liquids when the osmotic delivery system 270 is located in its environment of use. This may be achieved by cutting through the liquid impermeable sleeve 280, but not the semipermeable body 232, and then removing the portion of the sleeve directly adjacent to the cut. Thus, the exposure surface will then include the end surface and a portion of the exterior cylindrical surface 238. Increasing the amount of exposure surface area will increase the liquid permeation rate through the semipermeable body 232.

In the above described manner, the liquid permeation rate through the semipermeable body 232 can be controlled. Although not illustrated, the semipermeable body assembly 230 may also be configured with a recess and insert like the plug 30 illustrated in FIG. 7. This is further advantageous because a low liquid uptake membrane material can be used for the semipermeable body 232, while still permitting the liquid permeation rate to be controlled.

Figure 14:
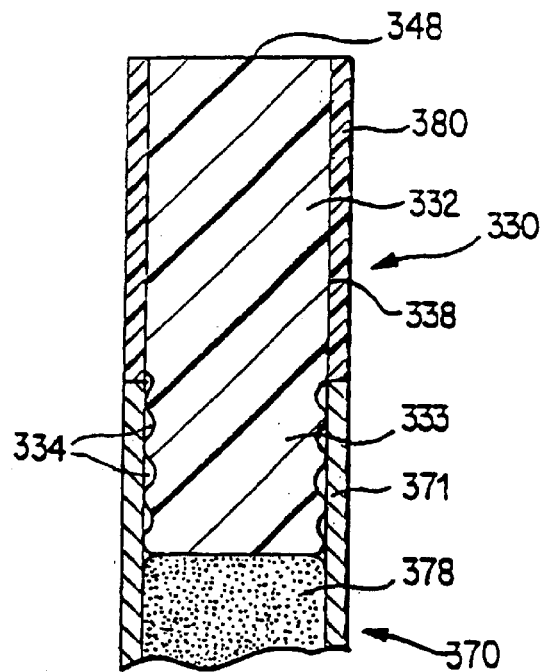
FIG. 14 is a partial sectional view of another osmotic delivery system according to the present invention having a semipermeable body and liquid impermeable sleeve, where only the semipermeable body has been inserted into the enclosure of the osmotic delivery system.

FIG. 14 illustrates another embodiment of an osmotic delivery system 370. As illustrated in FIG. 14, the osmotic delivery system 370 includes an elongated cylindrical enclosure 371 having an opening through which a semipermeable body assembly 330 has been inserted. The semipermeable body assembly 330 includes the semipermeable body 332 and the liquid impermeable sleeve 380, similar to the semipermeable body 232 and liquid impermeable sleeve 280 illustrated in FIG. 13. The enclosure 371 receives the osmotic agent 378, which drives the osmotic flow of the osmotic delivery system 370.

As illustrated in FIG. 14, only the semipermeable body 332 has been inserted into the opening of the enclosure 371. The liquid impermeable sleeve 380 is not located within the enclosure 371 because it has not been inserted in the opening of the enclosure. The osmotic agent 378 is directly adjacent to, or abuts against, the semipermeable body 332. The semipermeable body 332 allows liquid to pass from an environment of use into the enclosure 371 to cause the osmotic agent 378 to swell. The semipermeable body 332 and the liquid impermeable sleeve 380 together define an osmotic delivery system semipermeable body assembly 330 that controls a delivery rate of beneficial agent from the osmotic delivery system 370. The configuration of the semipermeable body 332 and the liquid impermeable sleeve 380 dictates the liquid permeation rate through the semipermeable body, which generally controls the delivery rate of the beneficial agent (not illustrated) from the osmotic delivery system 370.

The semipermeable body 332 is cylindrically shaped, like the semipermeable body 232 illustrated in FIG. 13, and is sized such that it is matingly received by an opening in the enclosure 371. As illustrated in FIG. 14, the semipermeable body 332 includes a plug end 333 having a series of ridges or ribs 334 which form a seal with the interior surface of the enclosure 371. However, contrary to the osmotic delivery system illustrated in FIG. 13, the liquid impermeable sleeve 380 is not inserted into the enclosure 371. The liquid impermeable sleeve 380 is located outside of the enclosure 371. The liquid impermeable sleeve 380 abuts against the exterior surface 338 of the semipermeable body 332 such that the cylindrical exterior surface 338 of the semipermeable body 332 is not immediately exposed to liquid when the osmotic delivery system 370 is located in the liquid environment of use. Liquid from the environment of use is also not allowed to substantially penetrate the joint between the sleeve 380 and the enclosure 371. Because the liquid impermeable sleeve 380 is not inserted into the enclosure 371, the semipermeable body 332 alone operates like a cork or stopper when it is inserted into the enclosure 371 of the osmotic delivery system 370, similar to the plug 30 illustrated in FIG. 7.

Like the liquid impermeable sleeve 280, the liquid impermeable sleeve 380 is separate from the enclosure 271, and surrounds only a portion of the entire peripheral surface of the semipermeable body 332 such that a portion of the peripheral surface is not immediately exposed to liquid when the osmotic delivery system is located in the liquid environment of use. Because the liquid impermeable sleeve 380 does not abut against the entire peripheral surface of the semipermeable body 332, the semipermeable body includes an exposure or liquid contact surface 348 defined by an area of the peripheral surface that is not surrounded by the liquid impermeable sleeve 380 and is located outside of the enclosure 371. The exposure surface 348 is immediately exposed to liquids when the osmotic delivery system 370 is located in the liquid environment of use.

The liquid permeation rate through the semipermeable body 332 of the osmotic delivery system 370 may be controlled or changed by varying the thickness of the semipermeable body 332. For example, the liquid permeation rate through the semipermeable body 332 may be changed to increase a delivery rate of the beneficial agent from the osmotic delivery system. The liquid permeation rate through the semipermeable body 332 may be increased by decreasing the thickness of the semipermeable body by, for example, cutting the semipermeable body. The semipermeable body 332 may be cut before or after it has been inserted into the enclosure 371. When cutting the semipermeable body 332, the liquid impermeable sleeve 380 may also be cut. That is, both the liquid impermeable sleeve 380 and the semipermeable body 332 may be cut in one action to decrease the thickness of both the liquid impermeable sleeve and the semipermeable body 332 in the longitudinal direction of the semipermeable body, i.e., parallel with the cylindrical exterior surface 338 of the semipermeable body 332.

The liquid permeation rate through the semipermeable body 332 may also be controlled by increasing the amount of surface area of the semipermeable body that is immediately exposed to liquids when the osmotic delivery system 370 is placed in its environment of use. The liquid permeation rate may be increased by removing a portion of the liquid impermeable sleeve 380 such that the amount of exposure surface 348 that is exposed to liquids is increased.

The liquid impermeable sleeve 380 can be fixed to the semipermeable body 332 by an adhesive or other means that prevent the sleeve from moving relative to the semipermeable body 332. Alternatively, the sleeve 332 can be movable relative to the body 332, although still contacting the cylindrical exterior surface 338 of the semipermeable body 332.

FIG. 15 illustrates another embodiment of an osmotic delivery system 470 according to the present invention. The osmotic delivery system 470 includes an enclosure 471 having an opening through which a semipermeable body 432 of a semipermeable body assembly 430 has been inserted. The semipermeable body 432 is similar to the semipermeable body 332 illustrated in FIG. 14 as the semipermeable body 432 includes a plug end 433 that has been inserted into the enclosure 471. Thus, only a portion of the semipermeable body 432 has been inserted into the enclosure 471. The semipermeable body 432 allows liquid to pass from an environment of use into the enclosure 471 to cause the osmotic agent 478 to swell and move the piston 474. The semipermeable body 432 and the liquid impermeable sleeve 480 together define the semipermeable body assembly 430 that controls a delivery rate of beneficial agent from the osmotic delivery system 470. The configuration of the semipermeable body 432 and the liquid impermeable sleeve 480 dictates the liquid permeation rate through the semipermeable body 432, which generally controls the delivery rate of the beneficial agent from the osmotic delivery system 470.

The liquid impermeable sleeve 480 is tubular, and abuts against the cylindrical exterior surface 438 of the cylindrical semipermeable body 432. In the embodiment of the present invention illustrated in FIG. 15, the liquid impermeable sleeve 480 is not inserted within the enclosure 471, and is thus located outside of the enclosure. The liquid impermeable sleeve 480 is fixedly attached to the exterior surface of the enclosure 471 as well as the exterior surface of the semipermeable body 432. The liquid impermeable sleeve 480 is fixedly attached to the semipermeable body 432 such that the liquid impermeable sleeve and the semipermeable body are not movable with respect to each other. The liquid impermeable sleeve 480 may be fixed to the semipermeable body 432 by an adhesive, weld, bonding agent or other similar device for securing or fastening the sleeve to the body.

The liquid impermeable sleeve 480 also forms a seal between the enclosure 471 and the sleeve 480 when the liquid impermeable sleeve 480 is positioned over the enclosure 471 and is affixed to the exterior surface of the enclosure. Thus, the liquid impermeable sleeve 480 is also not movable relative to the enclosure 471. Because the liquid impermeable sleeve 480 forms a seal or a watertight joint with the enclosure 471, the semipermeable body 432 need not include the plug end 433. In such an embodiment, the semipermeable body 432 is located entirely outside of the enclosure 471, and the seal between the liquid impermeable sleeve 480 and the enclosure 471 prevents liquid and other substances in the environment of use, besides the permeation liquid, from entering the osmotic delivery system 470 while also preventing materials from the inside of the delivery system from leaking or escaping to the environment of use.

The liquid permeation rate through the semipermeable body 432 may be increased by changing the thickness of the semipermeable body 432 and thus the liquid permeation rate through the semipermeable body, similar to the embodiments illustrated in FIGS. 13 and 14. For instance, the semipermeable body 432 may be cut to increase the liquid permeation rate through the semipermeable body.

FIG. 16 illustrates another embodiment of an osmotic delivery system 570. As illustrated in FIG. 16, the osmotic delivery system 570 includes an elongated cylindrical enclosure 571 having an opening through which a semipermeable body 532 has been inserted. The semipermeable body 532 is a cylindrical plug of semipermeable material having a series of ridges or ribs to help effect a seal between the semipermeable body 532 and the interior surface of the liquid impermeable enclosure 571. The enclosure 571 also receives the osmotic agent 578, which drives the osmotic flow of the osmotic delivery system 570 by moving the piston 574.

The semipermeable body 532 is not surrounded by a liquid impermeable sleeve that is separate and distinct from the enclosure 571. The semipermeable body 532 is only surrounded by the enclosure 571, similar to the semipermeable body 32 shown in FIG. 7. However, the enclosure 571 includes a plurality of grooves, channels, furrows, recesses or indentations 581 which define predetermined cutting locations by which an administrator can decrease the length of the enclosure 571 and the thickness of the semipermeable body 532. That is, the semipermeable body 532 surrounded by the enclosure 571 may be cut to increase the liquid permeation rate through the semipermeable body, i.e., the "effective thickness" L of the semipermeable body 532 is decreased. In this manner, the liquid permeation rate through the semipermeable body 532 may be varied to control the beneficial agent delivery rate from the osmotic delivery system 570.

As illustrated in FIG. 16, the indentations or grooves 581 define a plurality of 360° recesses that each lie on a plane approximately perpendicular to the longitudinal axis of the enclosure 571 (parallel with the exterior surface of the semipermeable body 532). An administrator may cut the enclosure 571 and the semipermeable body 532 along a plane that includes one of the grooves 581 such that the surface area of the exposure surface 548 will remain constant. By keeping the surface of the exposure surface 548 constant, the increase in liquid permeation rate through the semipermeable body 532 may be easily estimated when an administrator decreases the length of the semipermeable body 532 by cutting completely through one of the grooves 581. For instance, each of the grooves 581 may correspond to a predetermined or desired liquid permeation rate and/or a predetermined or desired beneficial agent delivery rate from the osmotic delivery system 570. Thus, an administrator of the osmotic delivery system 570 may easily change the permeation rate through the semipermeable body by simply cutting or slicing the semipermeable body 532 and the enclosure 571 along one of the grooves 581. The exterior surface of the enclosure 571 may include indicia indicating a desired permeation rate that corresponds to the respective groove 581.

FIG. 17 illustrates another embodiment of an osmotic delivery system 670 according to the present invention. As illustrated in FIG. 17, the osmotic delivery system 670 includes an elongated cylindrical enclosure 671. The osmotic delivery system 670 includes the semipermeable body assembly 630 having the semipermeable body 632 and liquid impermeable sleeve 680. As illustrated in FIG. 17, the semipermeable body 632 and the liquid impermeable sleeve 680 are both outside of the enclosure 671. The semipermeable body 632 is not positioned within the enclosure 671, and is larger than the opening into the enclosure 671 such that it may not be easily inserted into the enclosure. However, the osmotic delivery system 670 could be configured to receive a portion of the semipermeable body 632, such as illustrated in FIGS. 14 and 15. The enclosure 671 receives the osmotic agent 678 and the movable piston 674 and the osmotic agent 678 drives the osmotic flow of the osmotic delivery device 670.

As illustrated in FIG. 17, the semipermeable body 632 is located within the liquid impermeable sleeve 680 and the sleeve 680 is longer than the semipermeable body 632. The liquid impermeable sleeve 680 is threaded onto the enclosure 671 via the threads 682. The liquid impermeable sleeve 680 may include threads that engage the exterior surface of the enclosure 671, the enclosure may include threads that engage the interior surface of the liquid impermeable sleeve, or both the liquid impermeable sleeve and the exterior surface of the enclosure may include threads that matingly engage each other. Because the sleeve 680 is threadable onto and off of the enclosure 671, the liquid impermeable sleeve 680 is rotatable with respect to the enclosure 671. Thus, the liquid impermeable sleeve 680 may be moved linearly with respect to the enclosure 671 by rotating the sleeve with respect to the enclosure about the longitudinal axis of the enclosure via the threads 682. The liquid impermeable sleeve 680 may be moved longitudinally along the longitudinal axis of the enclosure 671, i.e., along an axis parallel with the cylindrical wall of the enclosure, by rotating the sleeve on the threads 682.

Because the diameter of the semipermeable body 632 is larger than that of the opening into the enclosure 671, when the liquid impermeable sleeve is threaded onto the enclosure 671 such that the liquid impermeable sleeve moves linearly toward the enclosure, the surface area of exposure surface 648 will increase, i.e., the peripheral surface area of the semipermeable body that is not touching or contacting the liquid impermeable sleeve will increase. Thus, the surface area of the semipermeable membrane body 632 that is immediately exposed to liquids when the osmotic delivery system is located in its environment of use may be increased by threading the liquid impermeable sleeve 680 onto the enclosure 671 such that the sleeve 680 moves with respect to the semipermeable body 632 and the enclosure 671.

The semipermeable body 632 is positioned within the liquid impermeable sleeve 680 such that the liquid impermeable sleeve may move relative to the semipermeable body 632. For example, the liquid impermeable sleeve 680 may receive the semipermeable body 632 and an interference fit manner sufficiently tight to retain the semipermeable body 632 within the liquid impermeable sleeve, while permitting the liquid impermeable sleeve 680 to slidingly move relative to the semipermeable membrane when the liquid impermeable sleeve is threaded onto the enclosure 671. However, the portion of the liquid impermeable sleeve 680 that abuts against the cylindrical exterior surface of the semipermeable body 632 is not immediately exposed to liquid when the osmotic delivery system 670 is located in a liquid environment of use. When the liquid impermeable sleeve 680 is threaded onto the enclosure 671, the exposure surface 648 will include more than the flat surface of the semipermeable body that is perpendicular to the liquid impermeable sleeve 680. For example, as the liquid impermeable sleeve 680 is threaded onto the enclosure 671 such that it moves toward the enclosure 671, a portion of the cylindrical exterior surface 638 of the semipermeable body 632 may be exposed to increase the liquid permeation rate through the semipermeable body 632.

Figure 18:
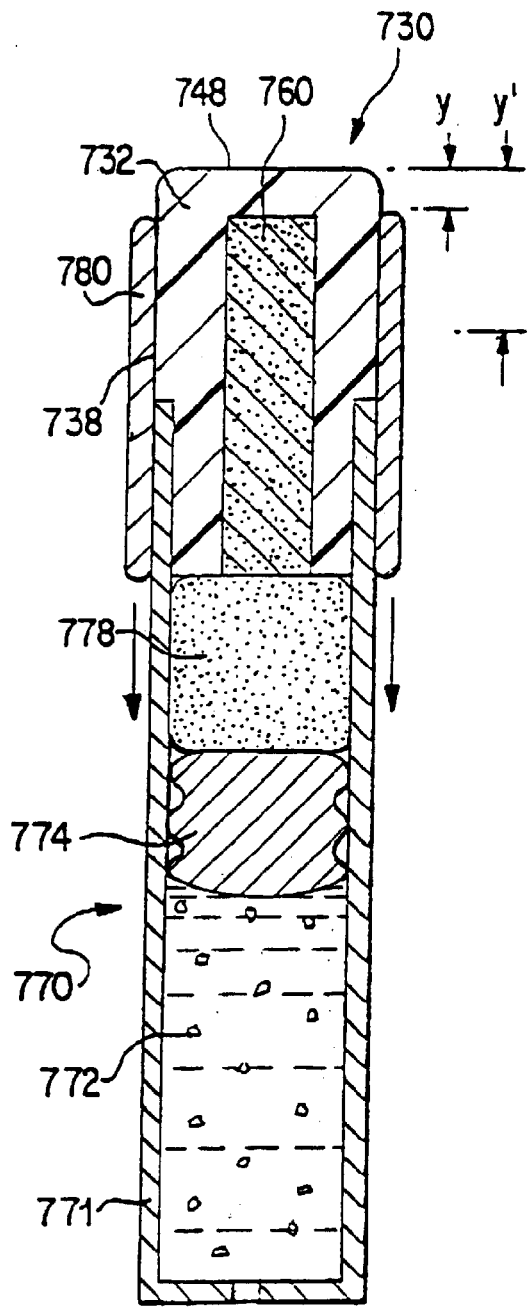
FIG. 18 is a sectional view of another osmotic delivery system according to the present invention having a semipermeable body and a liquid impermeable sleeve, where the liquid impermeable sleeve is slidable with respect to the enclosure of the osmotic delivery system.

By threading the liquid impermeable sleeve 680 toward the enclosure 671, an administrator may increase the surface area of the semipermeable body that is exposed to liquids when the osmotic delivery system 670 is placed in its environment of use. After the sleeve 680 has been moved toward the enclosure 671, the exposure surface 648 will thus be cap-shaped, rather than flat. Thus, it is apparent that the liquid permeation rate through the semipermeable body 632 may be varied by changing the exposure surface area of the semipermeable body. FIG. 18 illustrates another embodiment of the present invention that operates under a similar principle.

As illustrated in FIG. 18, the osmotic delivery system 770 includes an elongated substantially cylindrical enclosure 771 having an opening through which a semipermeable body 732 has been inserted. The semipermeable body 732 is part of a semipermeable body assembly 730 that includes the liquid impermeable sleeve 780. Within the enclosure 771 of the osmotic delivery system 770 is the beneficial agent 772 to be delivered, and a movable piston 774. The osmotic agent 778 within the enclosure 771 is separated from the beneficial agent 772 by the movable piston 774. The enclosure 771 receives the osmotic agent 778, which drives the osmotic flow of the osmotic delivery system 770.

As illustrated in FIG. 18, the osmotic delivery device 770 includes the semipermeable body 732 and the liquid impermeable sleeve 780. The semipermeable body 732 includes an insert 760, similar to the plug 30 illustrated in FIG. 7. Each of the semipermeable bodies 232, 332, 432, 632, 732, 832 illustrated in FIGS. 13–20 may include an insert that is received by a recess formed in the semipermeable body.

The semipermeable body 732 allows liquid to pass from an environment of use into the enclosure 771 to cause the osmotic agent 778 to swell. The semipermeable body 732 and the liquid impermeable sleeve 780 together define an osmotic delivery system semipermeable body assembly 730 that controls the delivery rate of beneficial agent 772 from the osmotic delivery system 770. The configuration of the semipermeable body 732 and position of the liquid impermeable sleeve 780 dictates the liquid permeation rate through the semipermeable body, which generally controls the delivery rate of the beneficial agent 772 from the osmotic delivery system 770.

As illustrated in FIG. 18, the semipermeable body 732 is surrounded by the tubular liquid impermeable sleeve 780. The interior surface of the liquid impermeable sleeve 780 abuts against the cylindrical surface 738 of the semipermeable body 732 and the respective surfaces are movable relative to each other such that the interior surface of the liquid impermeable sleeve slides relative to the exterior surface of the semipermeable body 732. As in the previous embodiments of the present invention, the liquid impermeable sleeve 780 abuts against the exterior surface of the semipermeable body 732 such that the surface area of the semipermeable body against which the liquid impermeable sleeve abuts is not immediately exposed to liquid when the osmotic delivery system is located in the liquid environment of use.

The liquid impermeable sleeve 780 is movable relative to the semipermeable body 732, as well as the enclosure 771 of the osmotic delivery system 770. For example, the liquid impermeable sleeve 780 is movable from the position Y to the position Y' with respect to the semipermeable body 732 along the longitudinal direction of the enclosure 771. In this manner, the amount of surface area of exposure surface 748 that is immediately exposed to liquids when the osmotic delivery system 770 is located in its environment of use may be increased. The liquid permeation rate through the semipermeable body 732 may be controlled by increasing the amount of surface area of the semipermeable body 732 that is exposed to liquids when the osmotic delivery system is placed in its environment of use. An administrator may move or slide the liquid impermeable sleeve 780 upward or downward relative to the enclosure 771 and the semipermeable body 732 to vary the liquid permeation rate through the semipermeable body 732.

In the embodiment of the present invention illustrated in FIG. 18, the liquid impermeable sleeve 780 is fitted to the enclosure 771 via a tight interference fit. The liquid impermeable sleeve 780 matingly engages the exterior surface of the enclosure 771 such that it may slide with respect to the exterior surface of the enclosure. Although the liquid impermeable sleeve 780 is fitted to the enclosure 771 via an interference fit, the liquid impermeable sleeve may also be movably fitted or movably attached to the enclosure 771 via other means. For example, the liquid impermeable sleeve 780 may be movably attached to the enclosure 771 through grooves, threads, or other similar devices. The exterior surface of the enclosure 771, the interior surface of the sleeve 780, or both the exterior surface of the enclosure and interim surface of the sleeve may include grooves, ridges, or lips to assist and control relative movement between the liquid impermeable sleeve 780 and the enclosure 771.

The semipermeable body 732 may be inserted into the opening of the enclosure 771, and, thereafter, the liquid impermeable sleeve 780 may be slid over the semipermeable body 732 and the enclosure 771 to a desired position that exposes an amount of exposure surface 748 that corresponds to a desired liquid permeation rate though the semipermeable body 732. Alternatively, the sleeve 780 may be slid over the semipermeable body 732 to a desired position that exposes an amount of exposure surface 748 that corresponds to a desired liquid permeation rate through the semipermeable body 732 before the semipermeable body assembly 730 is positioned in the enclosure 771. After the liquid impermeable sleeve 780 has been positioned to its desired location, an adhesive can be used to bond the liquid impermeable sleeve to the enclosure 771, such that it is no longer movable with respect to the enclosure 771 and the semipermeable body 732.

Figure 19:
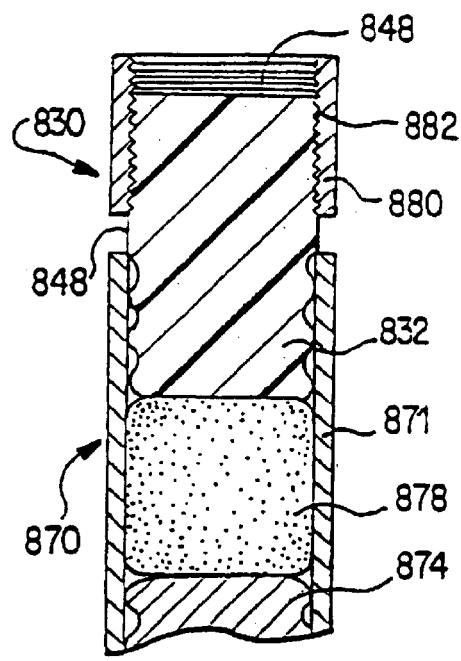
FIG. 19 is a partial sectional view of another osmotic delivery system according to the present invention having a semipermeable body and a liquid impermeable sleeve that is threaded on the semipermeable body and movable with respect to the semipermeable body.

FIG. 19 illustrates another embodiment of an osmotic delivery system 870 according to the present invention. As illustrated in FIG. 19, the semipermeable body assembly 830 includes a liquid impermeable sleeve 880 and a semipermeable body 832. The semipermeable body 832 has been inserted into the enclosure 871 of the osmotic delivery system 870. The semipermeable body 832 allows liquid to pass from an environment of use into the enclosure 871 to cause the osmotic agent 878 to swell and drive the piston 874. The osmotic agent 878 thus drives the osmotic flow of the osmotic delivery system 870. As illustrated in FIG. 19, the liquid impermeable sleeve 880 includes threads 882 on its interior surface. The liquid impermeable sleeve 880 is configured similar to a pipe or conduit that has threads on its interior surface. The threads 882 extend along the center axis of the liquid impermeable sleeve 880 such that the entire interior surface of the tubular sleeve includes the threads 882. Thus, the liquid impermeable sleeve 880 may be threaded onto the semipermeable body 832 via the threads 882. A portion of the semipermeable body 832 extends from the enclosure 871 such that the liquid impermeable sleeve 880 may be threaded onto the semipermeable body 832. The liquid impermeable sleeve 880 is separate from the enclosure 871 and abuts against or surrounds only a portion of the entire peripheral surface of the semipermeable body 832 such that at least a portion of the peripheral surface of the semipermeable body is not immediately exposed to liquid when the osmotic delivery system is located in a liquid environment of use.

The liquid permeation rate through the semipermeable body 832 may be controlled by increasing the amount of surface area of the semipermeable body that is immediately exposed to liquids when the osmotic delivery system 870 is placed in its environment of use. For example, the liquid permeation rate may be increased by partially unthreading or partially removing the liquid impermeable sleeve 880 from the portion of the semipermeable body 832 that extends from the enclosure 871. That is, the liquid permeation rate may be increased by increasing the exposed surface area of the semipermeable membrane body 832 that is immediately exposed to liquids when the osmotic delivery system is located in its environment of use. An administrator may partially unthread the liquid impermeable sleeve 880 from the semipermeable body 832 to increase the area of the exposure surface 848. As illustrated in FIG. 19, by partially unthreading the sleeve 880, the liquid contact surface or exposure surface 848 will include a portion of the cylindrical exterior surface of the semipermeable body 832 as well as the flat end surface of the semipermeable body 832 that is perpendicular to the cylindrical exterior surface of the semipermeable body. However, because the end surface is always exposed to liquids when the osmotic delivery system 870 is located in a liquid environment of use, the liquid permeation rate through the semipermeable body 832 is increased by increasing the amount of the cylindrical surface area of the semipermeable body that is immediately exposed to liquids when the osmotic delivery system 870 is located in its environment of use.

The liquid impermeable sleeve 880 can also be threaded onto the semipermeable body 832 to decrease the amount of cylindrical surface area of the semipermeable body that is immediately exposed to liquids when the osmotic delivery system is located in its environment of use. The liquid permeation rate through the semipermeable body 832 may be decreased by threading the liquid impermeable sleeve 880 onto the semipermeable body 832 to decrease an amount of cylindrical surface area that is immediately exposed to liquid when the osmotic delivery system is located in its environment of use. Although the liquid impermeable sleeve includes the threads 882, alternative means for fastening the liquid impermeable sleeve 880 to the semipermeable body 832 are contemplated. For example, the liquid impermeable sleeve 880 may fit onto the semipermeable body 832 via an interference fit. However, the sleeve 880 preferably does not overly compress the semipermeable body 832 such that the liquid permeation rate through the semipermeable body is affected.

The osmotic delivery system 870 may come assembled with the semipermeable body 832 extending from the enclosure 871, and an administrator may choose a liquid impermeable sleeve 880 that may fit over the semipermeable body 832 to vary the liquid permeation rate through the semipermeable body in the above-described manner. An administrator of the osmotic delivery system 870 may control the liquid permeation rate and hence the beneficial agent delivery rate from the osmotic delivery system 870 by simply varying the amount of surface area that is exposed to liquids when the osmotic delivery system is located in its environment of use. An adhesive or other means may be used to secure the liquid impermeable sleeve 880 to the semipermeable body after it has been moved to its desired position relative to the exterior surface of the semipermeable body 832. As described above, by varying the amount of surface area that is immediately exposed to liquids when the osmotic delivery system 870 is located in its environment of use, the liquid permeation rate through the semipermeable body 832 can be varied to control the beneficial agent delivery rate from the osmotic delivery system 870. The thickness of the liquid impermeable sleeve 880 and/or the semipermeable body 832 may also be decreased to change the liquid permeation rate through the semipermeable body.

Figure 20:
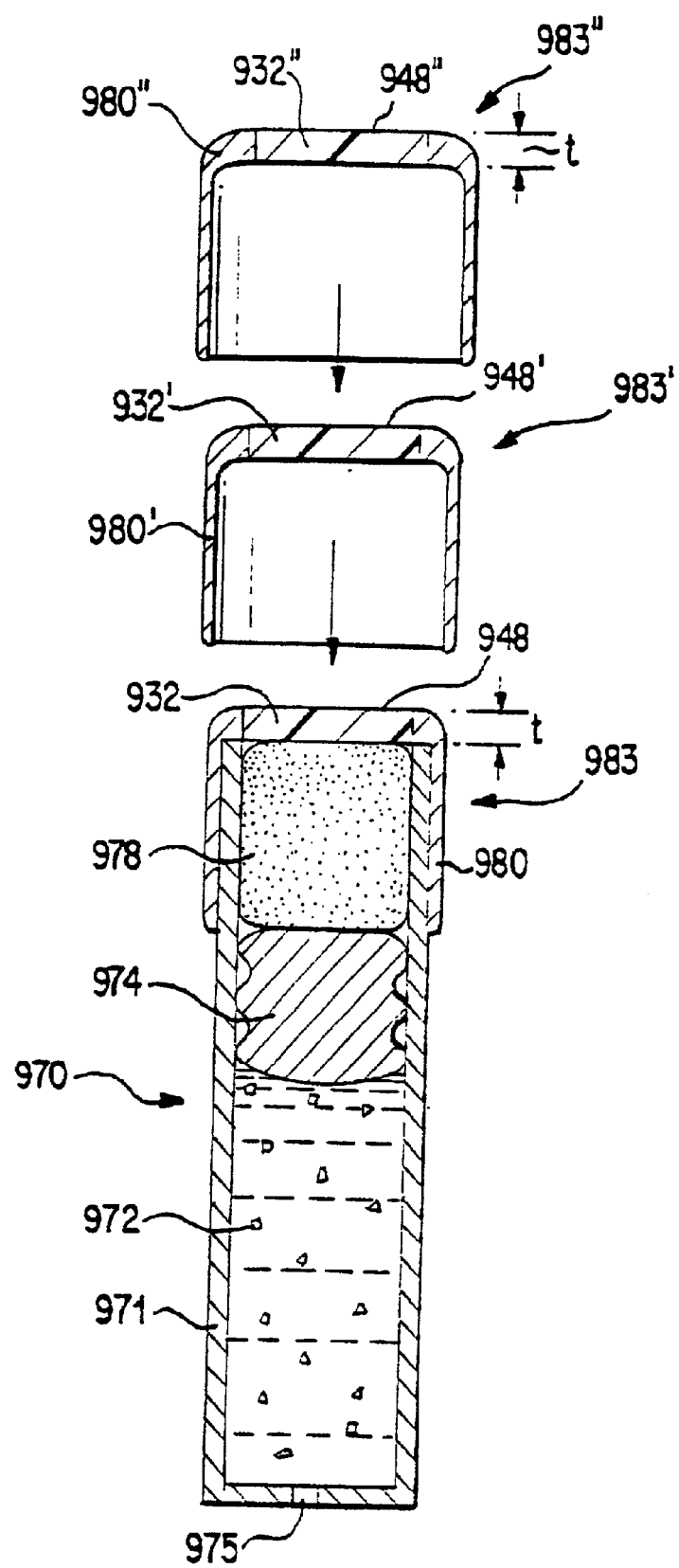
FIG. 20 is an exploded sectional view of another osmotic delivery system according to the present invention having a plurality of semipermeable bodies that are stackable upon each other.

FIG. 20 illustrates another embodiment of an osmotic delivery system 970 according to the present invention. The osmotic delivery system 970 includes an elongated substantially cylindrical enclosure 971 having an opening through which an osmotic agent 978, in the form of a tablet, and a piston 974 have been inserted. The osmotic delivery system 970 includes a first semipermeable body 932, as well as an optional second semipermeable body 932' and an optional third semipermeable body 932". The first semipermeable body 932, and optionally the second and third semipermeable bodies 932' and 932", respectively, are in liquid communication with the enclosure 971 such that liquids may permeate through the semipermeable bodies 932, 932', and 932" to the osmotic agent 978 and drive the osmotic flow of the osmotic delivery system 970. The end of the enclosure 971 opposite the opening through which the osmotic agent 978 has been inserted has one or more delivery ports 975 for delivering the beneficial agent 972 from the osmotic delivery system 970. The osmotic agent 978 within the enclosure 971 is separated from the beneficial agent 972 by the movable piston 974.

As illustrated in FIG. 20, the osmotic delivery device 970 includes at least the first semipermeable body 932. The first semipermeable body 932 is part of or integral with the first semipermeable body element 983. The first semipermeable body element 983 includes the first semipermeable body 932 as well as the wall portion 980. The wall portion 980 is a layer of liquid impermeable material that holds the first semipermeable body 932. The first semipermeable body 932 is not located within the opening of the enclosure 971. However, the semipermeable body 932 is generally directly adjacent or touching the osmotic agent 978.

The first semipermeable body 932 of the first semipermeable body element 983 allows liquid to pass from an environment of use into the enclosure 971 to cause the osmotic agent 978 to swell. The first semipermeable body 932 controls a delivery rate of beneficial agent 972 from the osmotic delivery system 970. More specifically, the thickness t and surface area of the exposure surface 948 of the semipermeable body 932 that is immediately exposed to liquids when the osmotic delivery system 970 is located in a liquid environment of use dictates the liquid permeation rate through the first semipermeable body 932, which generally controls the delivery rate of the beneficial agent from the osmotic delivery system 970.

As illustrated in FIG. 20, the first semipermeable body 932 is generally disc-shaped, such as a nickel or dime with one of its flat surfaces abutting against the osmotic agent 978 within the enclosure 971. The other flat surface defines the exposure surface 948. The first wall portion 980 of the first semipermeable body element 983 is tubular or cup-shaped and holds the first semipermeable body 932. The semipermeable body 932 generally defines the bottom of the cup-shaped semipermeable body element 983. The tubular wall portion 980 includes a recess that receives the enclosure 971.

The first semipermeable body 932 and the first wall portion 980 can be molded in a single operation to define a unified structure as the first semipermeable body element 983. Alternatively, the first semipermeable body 932 may be inserted into a preformed opening in the first wall portion 980 to form the semipermeable body element 983. A seal is located between the first semipermeable body 932 and the first wall portion 980 such that the interface is water-tight. The interior surface of the first wall portion 980 attaches to the exterior surface of the enclosure 971 such that the first semipermeable body 932, held by the first wall portion 980, is also attached to the enclosure 971.

Although the first wall portion 980 of the first semipermeable body element 983 illustrated in FIG. 20 is tubular, it may be other configurations. For example, the first wall portion 980 and first semipermeable body 932 may be rectangular and together define the shape of a rectangular adhesive bandage such as a BAND-AID® brand adhesive bandage. This configuration is particularly suitable for osmotic delivery systems that already include a semipermeable plug that seals the enclosure, such as that illustrated in FIG. 1. Such a semipermeable body element need not prevent materials from the exterior environment from entering the interior of the enclosure 971, as the semipermeable plug inserted in the enclosure of the osmotic delivery device already seals the enclosure from external materials, except for the permeation liquid.

The material forming the first wall portion 980 is liquid impermeable, similar to the liquid impermeable sleeves described above. The wall portion 980 is preferably formed from a material that is largely impermeable to the materials within the enclosure 971 and other ingredients within the environment of use. The wall portion 980 is preferably substantially impermeable to liquid in the environment of use as well as to ingredients contained within the osmotic delivery system 970 such that the migration of such materials into or out of the osmotic delivery system through the wall portion 980 is so low as to have substantially no adverse impact on the function of the osmotic delivery device. The wall portion 980 can also be formed from a flexible material such that it is conformable to the exterior surface of the enclosure 971.

The cylindrical interior surface of the first wall portion 980 that contacts the exterior surface of the enclosure 971 forms a seal with the exterior surface of the enclosure 971. The seal between the wall portion 980 and the enclosure 971 may be enhanced by threads or ribs in the interior surface of the wall portion 980 or the exterior surface of the enclosure 971. The seal between the first wall portion 980 and the enclosure 971 may be achieved by a tight interference fit, or an adhesive. Together, first the semipermeable body 932 and the first wall portion 980 of the first semipermeable body element 983 prevent liquid and other substances in the environment of use, besides the permeation liquid, from entering the osmotic delivery system 970 while also preventing materials from the inside of the delivery system from leaking or escaping to the environment of use.

As illustrated in FIG. 20, the osmotic delivery system 970 may include a plurality of semipermeable body elements 983, 983', 983". The semipermeable body elements 983, 983', 983" may be positioned in abutting relationship to one another to define a "net semipermeable body" of increased thickness to achieve a desired liquid permeation rate through the net semipermeable body. That is, an additional or second semipermeable body element 983' may be added to the osmotic delivery system 970 to achieve a different and desired liquid permeation rate. The second semipermeable body element 983' may be positioned adjacent to the first semipermeable body element 983 such that the second semipermeable body 932' is located in abutting or contacting relation to the first semipermeable body 932. Together, the first semipermeable body 932 and the second semipermeable body 932' form a net semipermeable body of the osmotic delivery system 970 having a liquid permeation rate different from that of the first semipermeable body 932 alone. For example, the liquid permeation rate through the net semipermeable body of the osmotic delivery system 970 may be decreased by increasing the "effective thickness" L of the net semipermeable body by providing two of the semipermeable bodies 932, 932' in abutting relation to one another. By positioning the second semipermeable body element 983' directly adjacent to the first semipermeable body element 983 such that the first and second semipermeable bodies 932, 932' contact, the second semipermeable body 932' is "stacked" or layered on the first semipermeable body 932 to define a net semipermeable body of greater thickness than either of the first and second semipermeable bodies alone. This may be achieved by positioning the second wall portion 980' of the second semipermeable body element 983' directly over the first wall portion 980 of the first semipermeable body element 983, similar to placing a first drinking cup on top of a second identical drinking cup such that the second cup receives the first cup.

The second wall portion 980' may be affixed or attached to the exterior surface of the first wall portion 980 of the first semipermeable body element 983 via an adhesive or other means for securing or attaching the second wall portion 980' to the first wall portion 980 enclosure 971. For example, the second wall portion 980' may be rigid and thread onto the first wall portion 980 or may be flexible and stretch over the first wall portion 980.

The thickness of the net semipermeable body may be further increased by positioning a third semipermeable body element 983" on top of the first and second semipermeable body elements 983, 983' such that the third semipermeable body 932" is adjacent and abutting the second semipermeable body 932'. By positioning the semipermeable bodies 932, 932', 932" in abutting relationship to one another, the semipermeable bodies are in liquid communication with each other so as to permit liquid to permeate through each of the semipermeable bodies 932, 932', 932" to the osmotic agent 978. For example, with an osmotic delivery system 970 that includes three abutting or layered semipermeable body elements 983, 983', 983", liquid from an external environment of use will first permeate through the third semipermeable body 932" to the second semipermeable body 932' and eventually through the first semipermeable body 932 such that the osmotic agent may swell and drive the osmotic flow of the osmotic delivery system 970.

Conversely, if the assembled osmotic delivery system 970 includes a plurality of stacked semipermeable body elements 983', 983", the liquid permeation rate through the net semipermeable body of the system may be increased by removing one or more of the semipermeable body elements 983, 983', 983". For example, should the osmotic delivery system 970 include three semipermeable body elements 983, 983', 983", the liquid permeation rate through the system may be increased by removing the third semipermeable body element 983" such that the thickness of the net semipermeable body of the system is decreased.

As described above, the stacked semipermeable body elements 983, 983', 983" form layers of semipermeable bodies 932, 932', 932". By removing or adding layers, the liquid permeation rate through the net semipermeable body of the system 970 may be controlled or varied. When the semipermeable bodies 932, 932', 932" are stacked or layered as described above, the semipermeable bodies 932, 932', 932" are in liquid communication with the liquid impermeable enclosure 971 to permit liquid from the environment of use to permeate through all of the semipermeable bodies to the osmotic agent 978 within the enclosure 971.

If the wall portions 980, 980', 980" are made of a resilient or flexible material, the semipermeable body elements 983, 983', 983" can be of identical construction while still stackable on each other such that only one semipermeable body element need be manufactured. Thus, a variety of liquid permeation rates may be achieved by stacking identical semipermeable body elements 983, 983', 983".

Although not illustrated, the second and third semipermeable body elements 983', 983" may include a semipermeable body 932', 932" that has a greater exposure surface area than that of the first semipermeable body 932. Likewise, the thicknesses of the second and third semipermeable bodies 932', 932" in the axial or longitudinal direction of the enclosure 971 may vary. Thus, the net thickness and the net exposure surface area A of the net semipermeable body of the osmotic delivery system 970 may be controlled by removing or adding semipermeable body elements 983 (983', 983") of different and varying configurations, i.e., having varying thicknesses and varying exposure surfaces 948, 948', 948".

The embodiments of the present invention illustrated in FIGS. 13–20 also allow an administrator to increase or decrease the release rate of beneficial agent from the osmotic delivery system. For example, just prior to subcutaneous placement in a human patient, the beneficial agent release rate of an osmotic delivery system according to the present invention may be adjusted to accommodate for the body weight of the patient. The beneficial agent release rate may be adjusted as part of the implantation procedure. Additionally, it may be adjusted after the osmotic delivery device has been implanted and a physiological or efficacious response has been determined. Thus, the osmotic delivery systems of the present invention may be used to obtain a specific therapeutic response as the beneficial agent release rate from the osmotic delivery systems is predictable and adjustable.

FIGS. 21–28 illustrate features of osmotic delivery system plugs or semipermeable body assemblies 1030, 1030', 2030, 2030' according to further embodiments of the present invention. The plugs 1030, 1030', 2030, 2030' each include a semipermeable body 1032, 1032', 2032, 2032' having a recess 1052, 1052', 2052, 2052' that can receive an insert, similar to the inserts 60, 160 described above in connection with the plugs 30, 130 illustrated in FIGS. 4 and 12.

The osmotic delivery system plugs 1030, 2030 will be described in reference to exemplary osmotic delivery systems 1070, 2070 according to embodiments of the present invention illustrated in FIGS. 25 and 28. The configuration of the osmotic delivery system plugs 1030, 2030 dictates the liquid permeation rate through the plugs, which generally controls the delivery rate of a beneficial agent 1072, 2072 from each of the osmotic delivery systems 1070, 2070.

Figure 21:
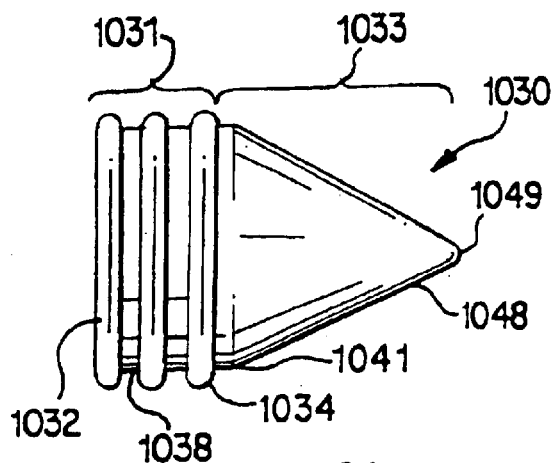
FIG. 21 is a side view of another osmotic delivery system plug or osmotic delivery system semipermeable body assembly according to the present invention.
Figure 22:
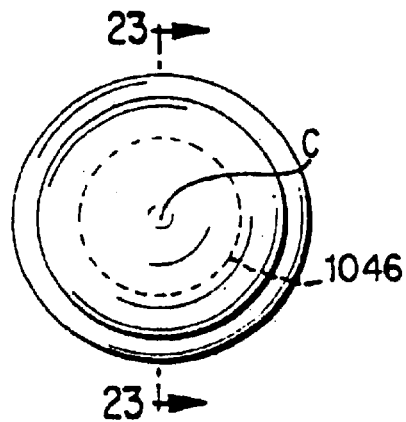
FIG. 22 is an end view of the osmotic delivery system plug of FIG. 21.

FIG. 21 illustrates a side view of the osmotic delivery system plug 1030. The plug 1030 is formed from a semipermeable body 1032. The semipermeable body 1032 includes a cylindrical portion 1031, and a conical portion 1033 located directly adjacent to the cylindrical portion 1031. The conical portion 1033 is in the shape of a right circular cone having a cone-shaped surface 1048, a vertex 1049, and a cone base 1041. The vertex 1049 of the cone-shaped surface 1048 is located opposite the cylindrical portion 1031 and the base 1041 of the conical portion. When positioned in the enclosure of an osmotic delivery system 1070, the vertex faces away from the osmotic agent 1078. As shown in FIG. 21, the vertex 1049 is a rounded or smoothed point.

The semipermeable body 1032 includes means for sealing or ribs 1034 that extend away from the outer surface 1038 of cylindrical portion 1031 of the plug 1030. The ribs 1034 are located at the cylindrical portion 1031 of the semipermeable body 1032. The ribs 1034 are the means by which the plug 1030 operates like a cork or stopper, obstructing and plugging an opening 1079 in the enclosure 1071 of the osmotic delivery system 1070 illustrated in FIG. 25. The semipermeable body 1032 is, therefore, intended for at least partial insertion into the opening 1079 of the enclosure 1071. The ribs 1034 seal the environment of use from an inside of the enclosure 1071 to prevent liquid and other substances in the environment of use, besides the permeation liquid, from entering the osmotic delivery system 1070 while also preventing materials from the inside of the delivery system from leaking or escaping to the environment of use.

Figure 24:
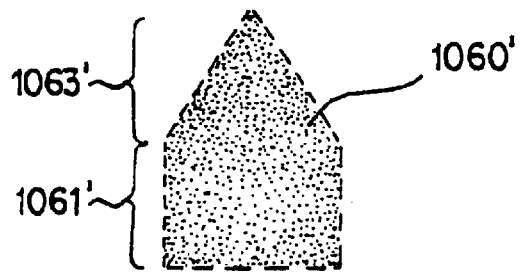
FIG. 24 is a side view of another insert of an osmotic delivery system plug according to the present invention.
Figure 25:
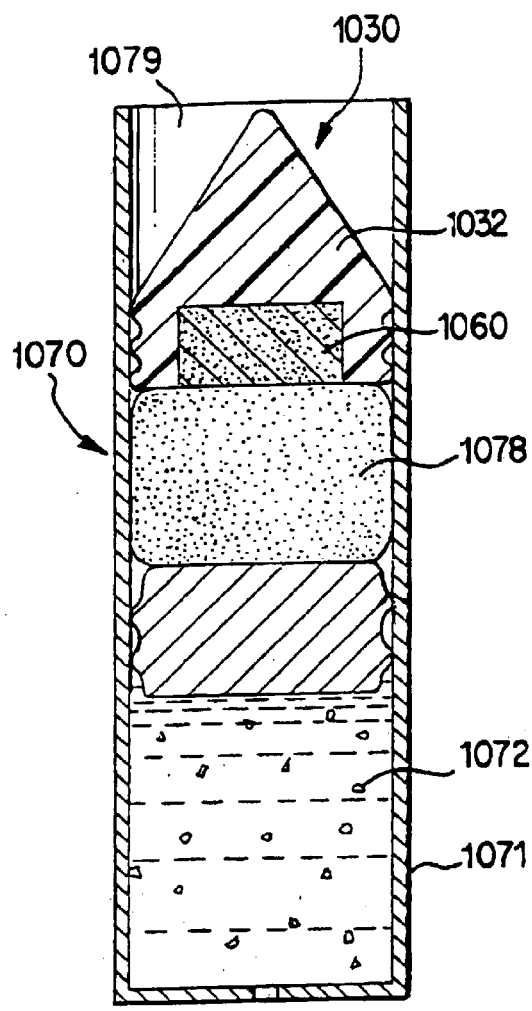
FIG. 25 is a sectional view of an osmotic delivery system according to the present invention having an osmotic delivery system plug according to FIG. 21.

As illustrated in FIGS. 21 and 25, the cylindrical portion 1031 having the ribs 1034 is intended for at least partial insertion in an osmotic delivery system opening 1079. The plug 1030 is partially or entirely insertable into the opening 1079. Because at least a portion of the plug 1030 is in contact with the interior surface of the enclosure 1071, and has means for sealing 1034, only a portion of the entire exterior surface of the semipermeable body 1032 is immediately exposed to liquids in the environment of use. In the embodiment of the present invention illustrated in FIGS. 21–25, the cone-shaped or conical surface 1048 of the conical portion 1033 is the exposure surface or liquid contact surface, i.e., that portion of the semipermeable body which is immediately exposed to liquids when the osmotic delivery system is placed in a liquid environment of use. Thus, the cylindrical portion 1031 is not immediately exposed to liquids when the osmotic delivery system 1070 is placed in a liquid environment of use, while the conical portion 1033 is immediately exposed to liquids when the osmotic delivery system 1070 is placed in a liquid environment of use.

Figure 26:
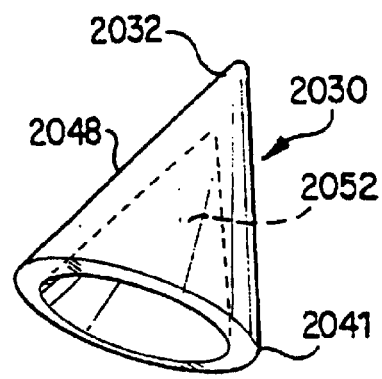
FIG. 26 is a perspective view of an osmotic delivery system plug according to the present invention, where the vertex of the cone-shaped plug has been tilted directly away from the viewer.

Although the osmotic delivery system plug 1030 includes the ribs 1034 to help form a seal between the enclosure 1071 and the semipermeable body 1032, other embodiments of the invention need not include the ribs 1034. For example, as illustrated in FIG. 26, the osmotic delivery system plug 2030 has a semipermeable body 2032 having an exterior surface 2048 that is smooth, entirely conical-shaped, and void of any ribs. In such an embodiment, an adhesive and/or an interference fit between the plug 2030 and the enclosure of the osmotic delivery system can be used to form the aforementioned seal between the enclosure and semipermeable body 2032. Thus, at least the base 2041 of the cone-shaped semipermeable body 2032 has a diameter that is greater than the internal diameter of the enclosure into which the body is to be inserted to help effect a seal between the semipermeable body and the enclosure. A portion of the conical exterior surface 2048 of the semipermeable body 2032 contacts the interior surface of the enclosure to define the seal between the enclosure and the semipermeable body. The portion of the conical exterior surface 2048 that contacts the interior surface of the enclosure 2071 is not immediately exposed to liquid when an osmotic delivery system incorporating the plug 2030 is located in a liquid environment of use. The portion of the conical exterior surface 2048 that does not contact the interior surface of the enclosure is immediately exposed to liquid when an osmotic delivery system incorporating the plug 2030 is located in a liquid environment of use.

Figure 27:
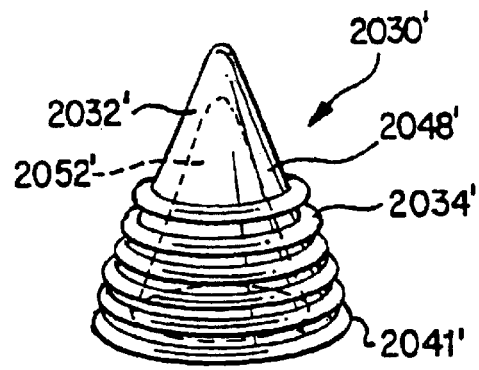
FIG. 27 is a perspective view of an osmotic delivery system plug according to the present invention, where the vertex of the cone-shaped plug has been tilted directly towards the viewer.

Additionally, it is not necessary that the osmotic delivery system plug 1030 include the cylindrical portion 1031. As illustrated in FIGS. 26 and 27, the osmotic delivery system plugs 2030, 2030' include a semipermeable body 2032, 2032' that is entirely cone-shaped.

As illustrated by FIG. 27, the conical-shaped semipermeable body 2032' may also include ribs 2034' on the conical exterior surface 2048' of the body. As shown in FIG. 28, a plurality of the ribs 2034' contact the interior surface of the enclosure 2071 when the semipermeable body 2032' is inserted into the opening of the enclosure of the osmotic delivery system 2070 according to another embodiment of the present invention. The base 2041' of the cone-shaped semipermeable body 2032, 2032' has a diameter that is greater than the internal diameter of the opening into the enclosure through which the body is to be inserted. Thus, as illustrated in FIG. 28, the base 2041' of the cone-shaped semipermeable body 2032' deflects when the semipermeable body is inserted into the enclosure 2071.

Figure 28:
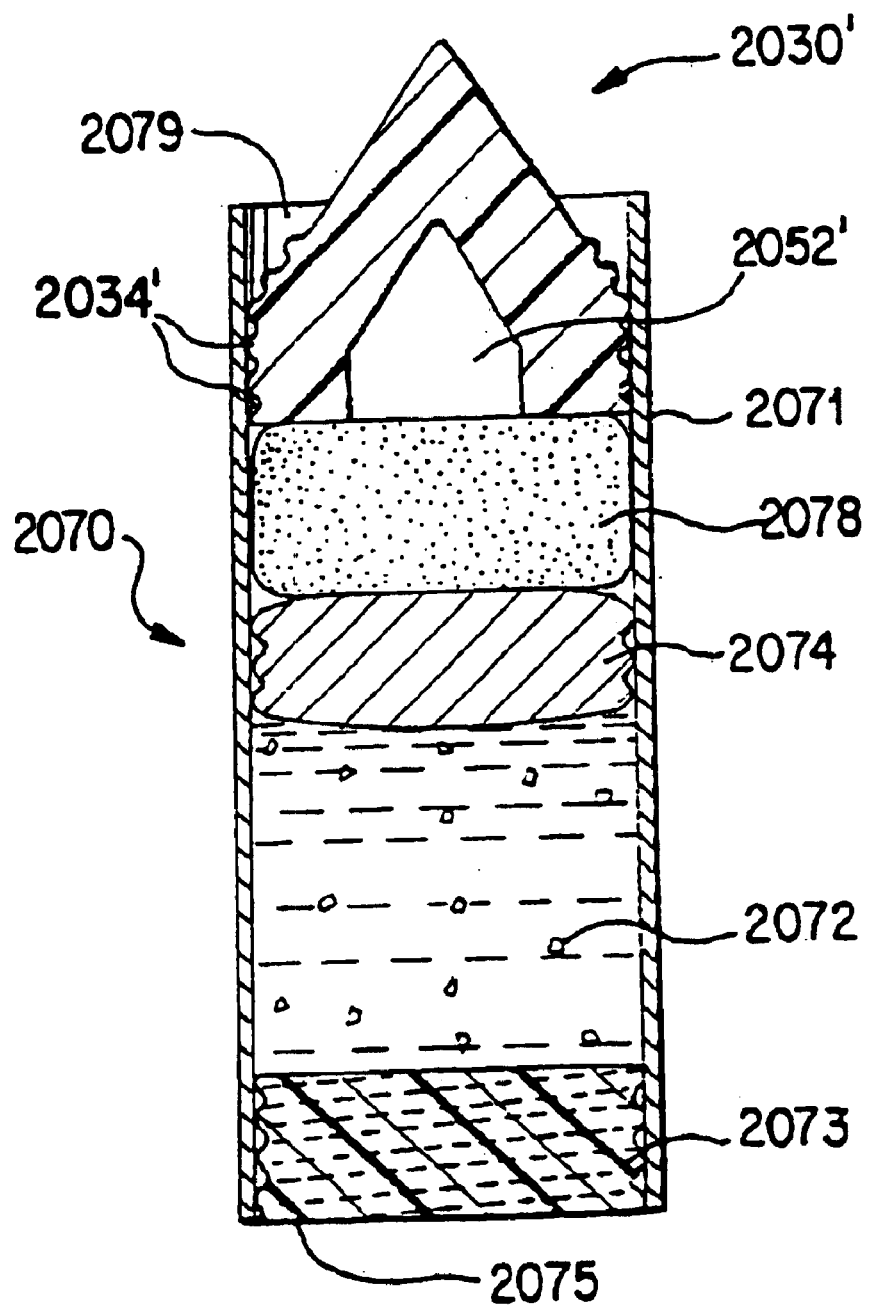
FIG. 28 is a sectional view of an osmotic delivery system according to the present invention having an osmotic delivery system plug according to FIG. 27.

The semipermeable bodies 2032, 2032' illustrated in FIGS. 26–28 include a conical recess or cone-shaped hollow portion 2052, 2052'. Because the base 2041, 2041' of the semipermeable body 2032, 2032' deflects when it is inserted into the enclosure 2071, the shape of the conical recess 2052, 2052' also changes. In the osmotic delivery system 2070, the semipermeable body 2032' has only been partially inserted into the enclosure 2071. Hence, a portion of the semipermeable body extends out of the enclosure 2071. The portion of the conical exterior surface 2048' that is not in contact with the enclosure 2071 and faces away from the osmotic agent 2078 will be immediately exposed to liquids when the osmotic delivery system 2070 is located in a liquid environment of use.

As shown in FIG. 25, the osmotic delivery system plug 1030 can be located entirely within the enclosure 1071 such that the cone-shaped surface 1048 is also located entirely within the enclosure 1071. The plug 1030 may be inserted entirely through an opening 1079 of the enclosure 1071 of the osmotic delivery system 1070 because the plug 1030 does not include a stop surface or head preventing complete insertion, such as the stop surface 36 illustrated in FIG. 2.

When the plug 1030 is completely inserted within the enclosure 1071 of the osmotic delivery system, the cone-shaped surface 1048 defines the liquid or exposure surface of the plug because it is immediately exposed to liquids when the osmotic delivery system 1070 is placed in a liquid environment of use. The plug 1030 may also be partially inserted into the opening 1079 of an osmotic delivery system enclosure 1071 such that a portion of the conical liquid contact surface 1048 is outside of the enclosure 1071.

As illustrated by the osmotic delivery system 2070 shown in FIG. 28, the delivery port 2075 is not directly formed in the wall of the enclosure 2071, but is instead located in a flow moderator or flow modulator device 2073. The flow modulator device 2073 is a plug-like member having a liquid flow path, such as the illustrated spiral delivery channel, through which beneficial agent can travel to exit the enclosure 2071. Such flow modulator devices are described in U.S. patent application Ser. No. 08/595,761, the entire disclosure of which is incorporated herein by reference. The flow modulator device 2073 closes-off one open end of a cylindrical tube to define the enclosure 2071. In this respect, the enclosure 2071 has a delivery port 2075.

As illustrated by FIG. 28, the cylindrical wall of the enclosure 2071 has two openings located opposite from each other and each configured to receive the flow moderator device 2074 and the osmotic delivery system plug 2030'. Thus, the enclosure 2071 includes a cylindrical tube having two opposing openings into the cylindrical tube. It will be appreciated that the plug 2030', as well as the previously described osmotic delivery system plugs 30, 130, 1030, 1030', 2030, can be inserted through either of the openings into the interior of the enclosure 2071. For example, in assembling the osmotic delivery system 2070 according to one embodiment of the present invention, the plug 2030' is inserted "vertex first" through an opening into the enclosure 2071. Once the osmotic agent 2078 has been formed, it is placed inside the enclosure 2071 through the same opening such that the tablet is adjacent to the plug 2030'. Then, the flow moderator device 2074 is inserted through the same opening so that the flow moderator device 2074 is on the side of the osmotic agent 2078 opposite from the plug 2030'. The enclosure 2071 is then filled with the beneficial agent 2072 and the flow moderator device 2073 is placed into the same opening of the enclosure 2071 to close off and seal the osmotic delivery system 2070.

Figure 23A:
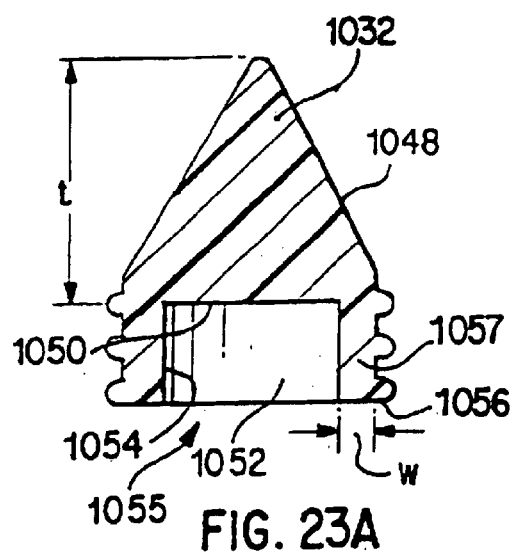
FIG. 23A is a sectional view of a semipermeable body of the osmotic delivery system plug according to the present invention taken along the line 23—23 of FIG. 22.
Figure 23B:
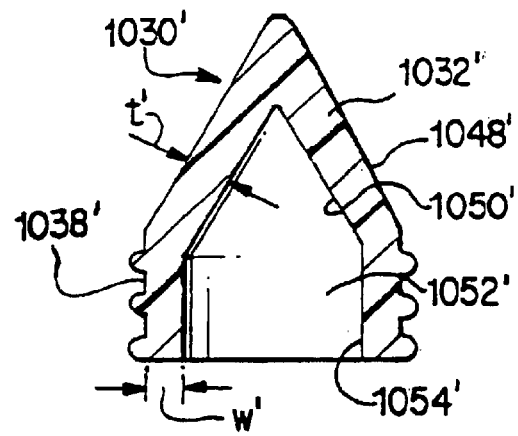
FIG. 23B is a sectional view of another semipermeable body of the osmotic delivery system plug according to the present invention taken along the line 23—23 of FIG. 22.

FIGS. 23A and 23B depict the cross-sections of semipermeable bodies 1032, 1032' according to the present invention. The semipermeable bodies 1032, 1032' each include a hollow interior portion or recess 1052, 1052'. In the embodiment of the present invention depicted in FIG. 23A, the recess 1052 is cylindrically shaped. The recess 1052 has a cylindrical and longitudinal interior surface 1054 which begins at an insert opening 1055 formed by the recess 1052 in the insert end 1056 of the semipermeable body 1032, and ends at a depth surface 1050 within the body 1032. Because of the cylindrical shape of the cylindrical portion 1031 of the semipermeable body 1032 and the cylindrical shape of the recess 1052, the body includes a cup-shaped region, where the "bottom of the cup" is conical and has a predetermined plug thickness t and the wall 1057 has a predetermined wall width w, similar to the plug 30 illustrated in FIG. 4B.

As shown in FIG. 23A, the predetermined wall width w is defined by the location of the outer surface 1038 relative to the interior surface 1054, and the predetermined plug thickness t is defined by the location of the depth surface 1050 relative to the conical surface 1048. Because the cone-shaped surface 1048 slopes relative to the depth surface 1050, the predetermined plug thickness t actually changes along the slope of the conical surface.

As described above in reference to the plug 30, the depth of the depth surface 1050 within the semipermeable body 1032, and the distance the interior surface 1054 is from the longitudinal center axis C (or diameter 1046 shown in FIG. 22 of the recess 1052) determine the size of the hollow recess 1052 in the interior of the semipermeable body 1032. Together, the predetermined wall width w and the predetermined plug thickness t define the effective thickness L of the semipermeable body 1032. As described above, by varying the size of the recess 1052, or, in other words, by varying the predetermined plug thickness t and/or the predetermined wall width w, the effective thickness L of the semipermeable body 1032 of the osmotic delivery system plug 1030 may also be varied. In this manner, the liquid permeation rate through the body 1032 can be controlled.

For instance, by decreasing the effective thickness L of the semipermeable body 1032 of the plug 30, the liquid permeation rate dV/dt through the plug may be increased. As illustrated in FIG. 23B, the effective thickness L of the semipermeable body 1032' may be decreased by decreasing the predetermined plug thickness t' of the semipermeable body. This is achieved by increasing the size of the recess 1052'.

FIG. 23B illustrates a preferred semipermeable body 1032'. The recess 1052' includes a cylindrical portion and a conical portion. Hence, the recess 1052' is in the shape of a bullet and has a volume greater than the cylindrical recess 1052. Alternatively, the recess 1052 can be entirely conical, such as the recesses 2052, 2052' shown in FIGS. 26 and 27. The recess 1052' generally follows the contours of the outer surface 1038' and cone-shaped surface 1048'. The distance of the depth surface 1050' relative to the cone-shaped surface 1048' is constant, and the distance of the outer surface 1038' relative to the interior surface 1054' is constant. Thus, the predetermined wall width w' and the predetermined plug thickness t' are approximately equal and constant. Although not illustrated, the semipermeable bodies 1032, 2032 need not include a recess or hollow portion.

FIGS. 24 and 25 illustrate inserts 1060, 1060' that can be included in an exemplary osmotic delivery plug 1030 or osmotic delivery system semipermeable body assembly in accordance with the present invention. As shown in FIG. 25, the insert 1060 is intended for insertion into the cylindrical recess or hollow interior portion 1052. The insert 1060 can be inserted in the recess 1052 for assisting the semipermeable body 1032 in effecting a seal with the interior of the enclosure 1071. In the embodiment of the present invention illustrated in FIG. 25, the insert 1060 is cylindrically shaped to match the shape of the recess 1052, similar to the insert 60 shown in FIGS. 5 and 6. The insert 1060 may be in any number of different shapes and sizes. For example, the insert can be entirely conical, or as illustrated by FIG. 24, the insert 1060' can be bullet-shaped. Thus, the insert 1060' includes a conical portion 1063' and a cylindrical portion 1061'. In the embodiments of the present invention illustrated in FIGS. 26 and 27, an insert (not illustrated) may be received by the recesses 2052, 2052'. As described above, because the semipermeable body 2032, 2032' will deflect upon insertion into the enclosure 2071, the insert can be volumetrically smaller than the recess 2052, 2052' and/or shaped differently than the recess 2052, 2052' to accommodate the deflection of the semipermeable body toward the interior of the enclosure 2071, while still assisting in effecting a seal between the enclosure and the semipermeable body 2032, 2032'. The insert 1060' shown in FIG. 24 can be received by a substantially identically shaped cone-shaped recess 1052'. The inserts 1060, 1060' can be fabricated from the same materials as the previously described insert 60.

Depending upon the application, the osmotic delivery system plugs 1030, 2030 need not include an insert. For example, in some circumstances and even if the semipermeable body includes a recess, the seal formed between the enclosure and the semipermeable body (without an insert therein) is sufficient to seal the environment of use from an inside of the enclosure to prevent liquid and other substances in the environment of use, besides the permeation liquid, from entering the osmotic delivery system while also preventing materials from the inside of the delivery system from leaking or escaping to the environment of use.

As described earlier, the beneficial delivery rate dMt/dt through a semipermeable body may be approximated by the following formula:

$$dMt/dt = dV/dt \cdot C = \{PA\Delta\pi/L\} \cdot C$$

For a selected membrane material, osmotic agent, and beneficial agent concentration, and thickness L, the liquid permeation rate dV/dt through the membrane is directly proportional to the liquid surface area A of the membrane body.

The liquid surface area $A_c$ of the conical surface 1048, 1048', 2048, 2048' is approximately, equal to $\pi r(r^2+h^2)^{1/2}$, where "r" is the radius at the base of the conical surface and "h" is the height of the conical surface.

When the osmotic delivery system plug 130 (see FIG. 12) is completely inserted into an opening of an enclosure of an osmotic delivery system, such as the opening 2079 shown in FIG. 28, the flat or end surface 148 is the liquid contact surface or exposure surface, i.e., the surface that is immediately exposed to liquid when the osmotic delivery system is located in its environment of use. The surface area $A_o$ of the flat or end surface 148 is equal to $\pi r^2$. In contrast, the surface area $A_c$ of the cone-shaped exterior surface 1048, 1048', 2048, 2048' is equal to $\pi r(r^2+h^2)^{1/2}$.

Figure 29:
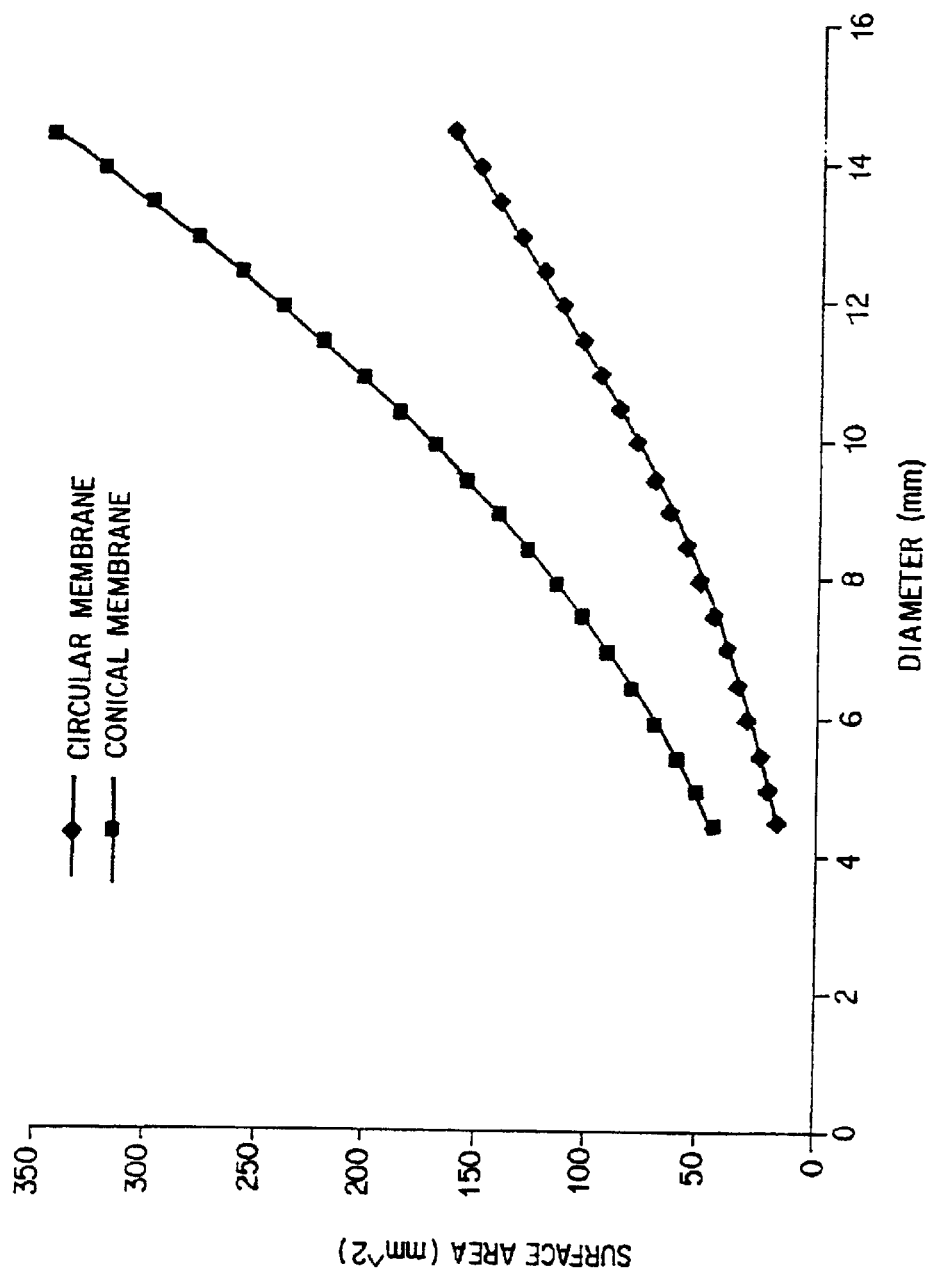
FIG. 29 is a graph illustrating the theoretical increase in surface area of a semipermeable membrane body having a conical surface as compared with a semipermeable membrane body having a flat circular surface, as the diameter of the membrane bodies correspondingly increase, where the thickness or height of the membrane bodies is equal.

One skilled in the art will appreciate that when the plugs 130, 1030 are completely inserted into openings of identical enclosures, the exposure surface area $A_c$ of the conical surface 1048 is greater than the exposure surface area $A_o$ of the flat or end surface 148 (assuming that the radius r, which generally corresponds to the internal diameter of the enclosure 1071, is the same for both semipermeable bodies). For example, FIG. 29 is a graph illustrating the theoretical increase in surface area $A_c$ (mm$^2$) for a conical surface of a semipermeable body (such as the conical surface 1048 of the semipermeable body 1032), and the theoretical increase in surface area $A_o$ (mm$^2$) for a flat circular surface of a semipermeable body (such as the flat circular surface 148 of the semipermeable body 132), as the diameter of the base of the conical surface and the diameter (mm) of the flat circular surface correspondingly increase. The curves illustrated in FIG. 29 are based on the above-described surface area equations for $A_c$ and $A_o$. As shown by FIG. 29, the surface area $A_c$ for the conical surface is greater than the surface area $A_o$ of the circular surface at all diameters.

Figure 30:
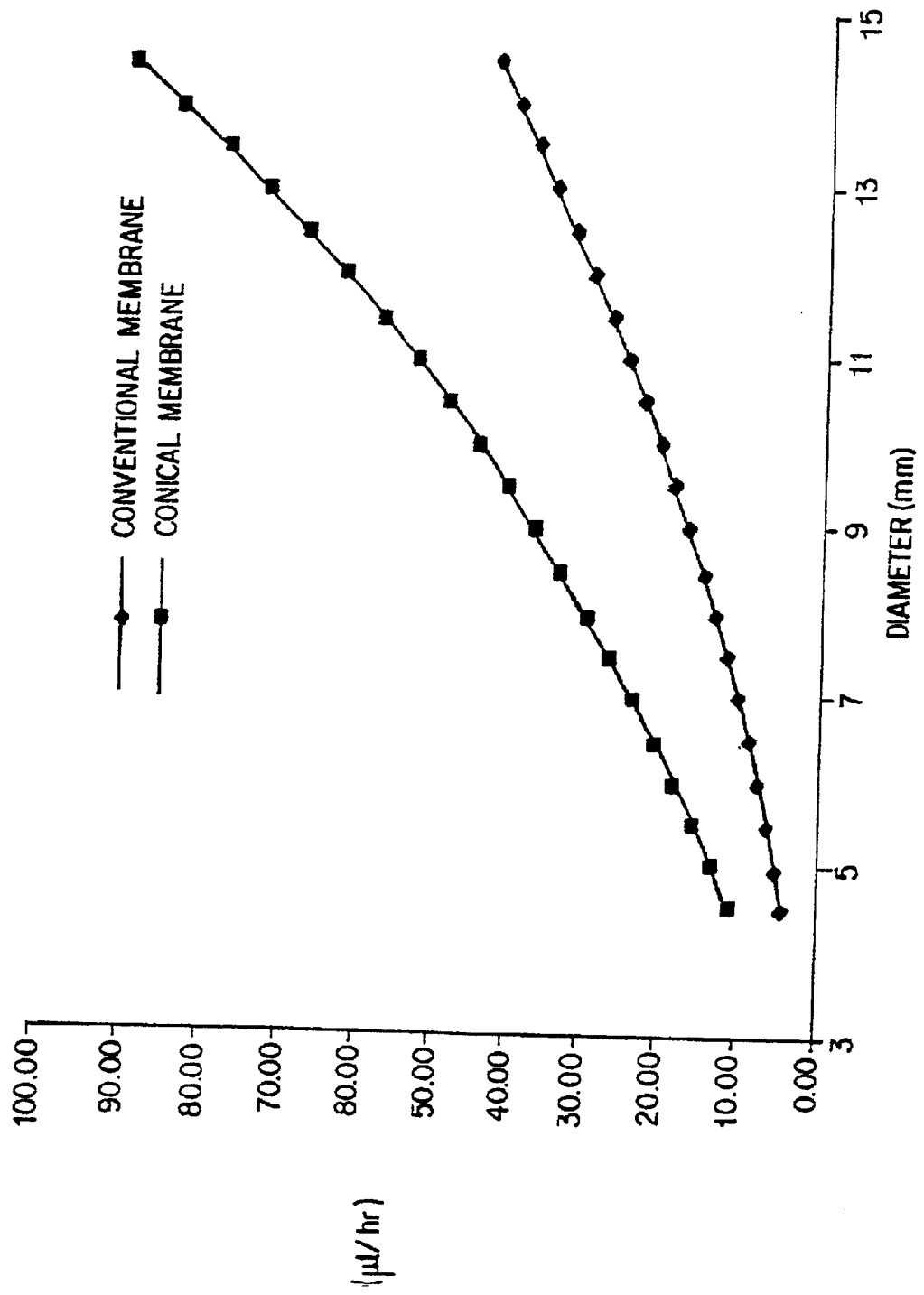
FIG. 30 is a graph illustrating the theoretical increase in the beneficial agent release rate of an osmotic delivery system, where the osmotic delivery system includes an osmotic delivery system semipermeable plug having a semipermeable body with a conical surface according to the present invention.

Because the surface area $A_c$ of the conical surface 1048 is greater than that of the flat circular surface 148, the liquid permeation rate through the semipermeable body 1032 will be greater than that through the semipermeable body 132 (assuming that the semipermeable bodies 132, 1032 have roughly the same effective thickness L). Accordingly, the liquid permeation rate through the semipermeable bodies of the present invention may be increased by increasing the surface area A of the semipermeable body that is immediately exposed to liquids upon insertion of the osmotic delivery system in a liquid environment of use. For example, FIG. 30 illustrates the theoretical increase in beneficial agent release rate dMt/dt (μl/hour) from an osmotic delivery system having a semipermeable body having a conical surface area $A_c$ (such as that illustrated in FIG. 23B) as the diameter of the semipermeable body increases. FIG. 30 also generally illustrates the actual increase in beneficial agent release rate dMt/dt (μl/hour) from an osmotic delivery system having a semipermeable body having a flat circular surface area $A_o$ (such as that illustrated in FIG. 12) as the diameter of the semipermeable body increases. The calculations used to obtain the curves shown in FIG. 30 assume that both semipermeable bodies are completely inserted within an enclosure of an osmotic delivery system.

The curve illustrated in FIG. 30 corresponding to the semipermeable membrane body having a flat circular surface area $A_o$ was obtained by testing an osmotic delivery system having a semipermeable membrane body similar to that illustrated in FIG. 12 (formed from PEBAX 23, having a 23 mil thickness, and a 10.5% radial clearance where radial clearance is the amount of pressure it takes to push the semipermeable membrane body out of the enclosure as measured by the ratio of the ID of the enclosure divided by the OD of the membrane expressed as a percentage). The curve illustrated in FIG. 30 corresponding to the semipermeable membrane body having a conical surface area $A_c$ was obtained by theoretically estimating how much the beneficial agent release rate dMt/dt would increase (based on the equations: $A_c = r(r^2+h^2)^{1/2}$ and $dMt/dt = dV/dt \cdot C = \{PA\Delta\pi/L\} \cdot C$) if the flat circular surface area $A_o$ were increased to the conical surface area $A_c$ as shown in FIG. 29 for a given diameter. As FIG. 30 illustrates, because the surface area $A_c$ of a conical surface is greater than that of a flat circle, the liquid permeation rate through a semipermeable body having a conical surface will be greater than that through a semipermeable body having only a flat circular surface. Accordingly, the liquid permeation rate through the semipermeable bodies of the present invention may be increased by increasing the surface area A of the semipermeable body that is immediately exposed to liquids upon insertion of the osmotic delivery system in a liquid environment of use.

The surface area A that is immediately exposed to liquids may be increased by manufacturing the exposure or liquid contact surface in a conical shape, a spherical shape, or other configurations that have a greater surface area than that of a flat disk. In this manner, the liquid permeation rate through the semipermeable membrane body may be further increased.

In many instances, it is desirable to increase the beneficial agent delivery rate dMt/dt from osmotic delivery systems. For example, osmotic delivery systems destined for animal implantation often must be able to release all of the beneficial agent within a short period of time, such as one week or even a few days. As described earlier, the beneficial agent delivery rate dMt/dt may be increased by increasing the osmotic pressure difference between the osmotic agent and the liquid on the other side of the membrane, and by varying the liquid permeability coefficient P of the semipermeable material. Depending upon the specific application, it may not be possible to further increase the beneficial agent delivery rate dMt/dt by varying the permeability coefficient P or the osmotic pressure difference $\Delta\pi$. Additionally, it may not be possible to further increase the liquid permeation rate through the semipermeable membrane (to increase beneficial agent delivery rate dMt/dt) by decreasing the effective thickness L of the semipermeable membrane body without jeopardizing the structural integrity and sealing characteristics of the semipermeable membrane body. Thus, in these circumstances it is desirable to increase the liquid permeation rate through the semipermeable body without substantially decreasing the effective thickness L of the semipermeable body.

As set forth above, the liquid permeation rate through the semipermeable membrane bodies of the present invention may be increased by increasing the surface area A of the semipermeable body that is immediately exposed to liquid when the osmotic delivery system is located in a liquid environment of use. For example, the exposure surface area A may be increased by forming the conical portion 1033 on the semipermeable body 1032. Because the exposure surface area $A_c$ of the cone-shaped surface 1048 is greater than the exposure surface area $A_o$ of the flat or end surface 148, the liquid permeation rate through the semipermeable membrane 1032 is greater than that of the semipermeable body 132. Hence, the beneficial agent delivery rate dMt/dt may be increased by increasing the surface area A of the semipermeable body that is immediately exposed to liquids when the osmotic delivery system is located in a liquid environment of use.

In the above described manner, the liquid permeation rate dV/dt through the membrane plugs 1030, 1030', 2030, 2030' can be increased, permitting faster beneficial agent delivery rates from osmotic delivery systems according to the present invention. This is further advantageous because low liquid uptake membrane materials can be used to fashion osmotic delivery system plugs 1030, 1030', 2030, 2030' according to the present invention with fast liquid permeation rates. Such fast permeation rates were previously achieved by fashioning membrane plugs from high liquid uptake and possibly biologically unstable membrane materials, which occasionally permit items in the interior of the osmotic delivery system to leak to the environment of use.

The osmotic delivery system plugs 1030, 1030', 2030, 2030' permit the administration of beneficial agents from osmotic delivery systems at rapid delivery rates over a relatively short period of time, even though the plugs may use a semipermeable material which, as measured against previous membrane plugs, has a low permeability coefficient. These low permeability coefficient membrane materials do not have high liquid uptake characteristics, and do not swell as dramatically as high uptake materials when liquid from the surrounding environment permeates through the membrane. Thus, the osmotic delivery plugs 1030, 1030', 2030, 2030', that each include a recess 1052, 1052', 2052, 2052' and a cone-shaped exterior surface 1048, 1048', 2048, 2048' configured for a fast liquid permeation rate, do not overly swell and creep out of the capsule, or permit the osmotic agent to leak from the capsule. Furthermore, the osmotic delivery plug 1030, 1030', 2030, 2030' can be made from materials that are stable in biological environments, and do not significantly degrade over time, which could permit fluids, crystals, or powder within the interior of the enclosure to leak to the environment of use.

Another benefit of controlling the surface area A, as well as the effective thickness L, of the osmotic delivery system plugs 1030, 1030', 2030, 2030' is that different liquid permeation rates are obtainable from the same semipermeable material having a set permeability coefficient. A different membrane material need not be used for every system which has a different desired beneficial agent delivery rate, and biocompatibility and toxicity tests need only be performed on one semipermeable material.

In the above described manner, the liquid permeation rate through the semipermeable bodies 32, 132, 232, 332, 432, 632, 732, 732', 832, 932, 932', 932", 1032, 1032', 2032, 2032' can be controlled in the osmotic delivery devices illustrated in FIGS. 7, 13–20, 25 and 28. This is especially advantageous because one membrane material can be used for the semipermeable bodies, while still permitting the liquid permeation rate to be controlled or varied. Additionally, as described above, by varying the "effective thickness" L and/or the exposure surface area A of the semipermeable bodies, the liquid permeation rate through the semipermeable bodies, and hence the delivery rate of the beneficial agent from the osmotic delivery system, can be controlled. This is beneficial because, for example, different desired liquid permeation rates through the semipermeable bodies are obtainable from semipermeable bodies formed from the same material having the same permeability coefficient and liquid uptake characteristics. This is further beneficial because biocompatibility and toxicity tests need only be performed on one semipermeable material. Moreover, it is especially desirable that the beneficial agent delivery rate from the osmotic delivery system be easily controlled by simply varying the liquid permeation rate through the semipermeable body of any one of the alternative embodiments of the present invention described above.

While the invention has been described in detail with reference to a preferred embodiment thereof, it will be apparent to one skilled in the art that various changes can be made, and equivalents employed without departing from the spirit and scope of the invention.

What is claimed is:

1. An osmotic delivery system plug for controlling a delivery rate of a beneficial agent in an osmotic delivery system comprising:
    a semipermeable body at least partially positionable in an opening in an enclosure of an osmotic delivery system, the semipermeable body including
        a cone-shaped, liquid contact surface for contacting a liquid outside of the osmotic delivery system; and
        a hollow interior portion having a size selected to obtain a predetermined liquid permeation rate through the semipermeable body, the liquid permeation rate for controlling a delivery rate of a beneficial agent in the osmotic delivery system.

2. The osmotic delivery system plug according to claim 1, wherein the hollow interior portion is conical.

3. The osmotic delivery system plug according to claim 1, wherein the hollow interior portion is cylindrical.

4. The osmotic delivery system plug according to claim 3, wherein the liquid contact surface is located at an end of the body opposite the hollow interior portion.

5. The osmotic delivery system plug according to claim 4, wherein the hollow interior portion includes a depth surface defining a plug thickness of the semipermeable body between the liquid contact surface and the depth surface.

6. The osmotic delivery system plug according to claim 1, including an insert located within the hollow interior portion.

7. The osmotic delivery system plug according to claim 6, wherein the hollow interior portion and the insert are cylindrical, the cylindrical hollow interior portion matingly receiving the cylindrical insert.

8. The osmotic delivery system plug according to claim 6, wherein the insert is pervious to liquids.

9. The osmotic delivery system plug according to claim 6, wherein the insert is a semipermeable material having a different permeability than that of the semipermeable body.

10. The osmotic delivery system plug according to claim 6, wherein the insert includes an osmotic agent.

11. The osmotic delivery system plug according to claim 6, wherein the insert has a longitudinal length substantially equal to a depth of the hollow interior portion.

12. The osmotic delivery system plug according to claim 6, wherein the insert has a size and shape which substantially matches a size and shape of the hollow interior portion of the semipermeable body.

13. The osmotic delivery system plug according to claim 1, wherein the semipermeable body includes an outer sealing surface for effecting a seal with the enclosure when the body is at least partially positioned in the enclosure.

14. The osmotic delivery system plug according to claim 13, wherein the hollow interior portion includes an interior surface defining a wall width between the outer sealing surface and the interior surface.

15. The osmotic delivery system plug according to claim 13, including a liquid pervious member located within the hollow interior portion for assisting in effecting the seal.

16. The osmotic delivery system plug according to claim 13, wherein the outer sealing surface includes at least one rib.

17. The osmotic delivery system plug according to claim 1, wherein the semipermeable body is a unitary, one piece member.

18. An osmotic delivery system comprising:
   an enclosure having an opening and a delivery port, the enclosure having an interior holding a liquid swellable osmotic agent and a beneficial agent, the liquid swellable osmotic agent for imbibing liquid from a surrounding environment and causing a delivery rate of said beneficial agent from the enclosure;
   a plug having a semipermeable body at least partially positioned in the opening, the semipermeable body including
      a cone-shaped, liquid contact surface for contacting a liquid outside of the osmotic delivery system; and
      a hollow interior portion having a size selected to obtain a predetermined liquid permeation rate through the semipermeable body, the liquid permeation rate for controlling a delivery rate of a beneficial agent in the osmotic delivery system.

19. The osmotic delivery system according to claim 18, further comprising a separating member positioned in the enclosure between the osmotic agent and the beneficial agent.

20. The osmotic delivery system according to claim 19, wherein the separating member is a movable piston.

21. The osmotic delivery system according to claim 18, wherein the osmotic agent is a tablet.

22. The osmotic delivery system according to claim 18, wherein the plug includes an insert located in the hollow interior portion of the semipermeable body.

23. The osmotic delivery system according to claim 18, wherein the enclosure is substantially impermeable to liquids.

24. The osmotic delivery system according to claim 18, wherein the semipermeable body includes a cone-shaped surface.

25. A method of controlling a delivery rate of a beneficial agent from an osmotic drug delivery system that includes an enclosure having an interior holding a liquid swellable osmotic agent and a beneficial agent, the osmotic drug delivery system also including a plug having a semipermeable body at least partially positioned in an opening of the enclosure, the semipermeable body including a hollow interior portion, the method comprising:
   determining a desired delivery rate of the beneficial agent;
   selecting a plug having a cone-shaped, liquid contact surface for contacting a liquid outside of the osmotic delivery system and having a hollow interior portion sized to obtain a predetermined liquid permeation rate through the semipermeable body corresponding to the desired delivery rate of the beneficial agent;
   positioning the plug at least partially within the opening of the enclosure; and
   locating the osmotic drug delivery system in an environment of use.

26. The method according to claim 25, further including:
   locating an insert within the hollow interior portion.

27. An osmotic delivery system comprising:
   an enclosure having an opening and a delivery port, the enclosure having an interior holding a liquid swellable osmotic agent and a beneficial agent, the liquid swellable osmotic agent for imbibing liquid from a surrounding environment and causing a delivery rate of the beneficial agent from the enclosure; and
   a plug having a semipermeable body, the plug being at least partially positioned in the opening, the semipermeable body having an exposure surface that is immediately exposed to liquids when the osmotic delivery system is located in a liquid environment of use, the exposure surface including a conical surface.

28. The osmotic delivery system according to claim 27, wherein the semipermeable body includes a cylindrical portion.

29. The osmotic delivery system according to claim 27, wherein a vertex of the conical surface faces away from the osmotic agent.

30. The osmotic delivery system according to claim 27, wherein the semipermeable body includes ribs for effecting a seal between the enclosure and the semipermeable body.

31. The osmotic delivery system according to claim 27, wherein the semipermeable body includes a hollow interior portion having a size selected to obtain a predetermined liquid permeation rate through the semipermeable body, the liquid permeation rate for controlling the delivery rate of the beneficial agent in the osmotic delivery system.

32. The osmotic delivery system according to claim 31, further comprising:
   a porous insert located in the hollow interior portion.

* * * * *